(12) United States Patent
Bieberich

(10) Patent No.: US 6,718,785 B2
(45) Date of Patent: *Apr. 13, 2004

(54) COOLING DEVICES WITH HIGH-EFFICIENCY COOLING FEATURES

(75) Inventor: Mark Thomas Bieberich, Edina, MN (US)

(73) Assignee: Arizant Healthcare Inc., Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/316,305

(22) Filed: Dec. 10, 2002

(65) Prior Publication Data

US 2003/0079488 A1 May 1, 2003

Related U.S. Application Data

(60) Continuation of application No. 10/016,934, filed on Dec. 13, 2001, now Pat. No. 6,519,964, which is a division of application No. 09/546,513, filed on Apr. 11, 2000, now Pat. No. 6,354,099.

(51) Int. Cl.[7] ............................. F25D 23/12; F28D 5/00; A61F 7/00
(52) U.S. Cl. .................... 62/259.3; 62/314; 607/104; 607/107
(58) Field of Search ................ 62/259.3, 314, 62/91, 457.1, 406, 530, 457.2, 424; 165/46; 607/96, 99, 104, 107, 108, 109

(56) References Cited

U.S. PATENT DOCUMENTS

| | | | |
|---|---|---|---|
| 4,867,230 A | | 9/1989 | Voss |
| 5,324,320 A | | 6/1994 | Augustine et al. |
| 5,384,924 A | | 1/1995 | Dickerhoff et al. |
| 5,405,370 A | * | 4/1995 | Irani ........................ 607/104 |
| 5,405,371 A | | 4/1995 | Augustine et al. |
| 5,658,325 A | | 8/1997 | Augustine |
| 5,722,482 A | | 3/1998 | Buckley |
| 5,733,318 A | * | 3/1998 | Augustine ................... 607/104 |
| 5,800,489 A | * | 9/1998 | Augustine ................... 607/107 |
| 5,860,292 A | | 1/1999 | Augustine et al. |
| 6,112,348 A | | 9/2000 | Dickerhoff |
| 6,354,099 B1 | * | 3/2002 | Bieberich .................. 62/259.3 |

* cited by examiner

Primary Examiner—Chen Wen Jiang
(74) Attorney, Agent, or Firm—INCAPLAW; Terrance A. Meador

(57) ABSTRACT

Cooling devices are provided to reduce a person's temperature by evaporative, convective, and/or conductive cooling. One such device maximizes evaporative cooling by aiding the flow of air to the person and the removal of vapor-laden air from the person. An upper sheet and a base sheet are adhered to define numerous elongated, parallel, inflatable cooling chambers separated by flat connecting membranes. Ventilating cross-members interconnect the cooling chambers. Air enters the chambers through an inlet, exits the chambers toward the person through air permeable regions of the base sheet. Air heated by the person's body exits the device upward through evaporation openings in the connecting membranes. The foregoing device, or different variations thereof, may be modified for use in conductive cooling by adding an absorbent sheet beneath the base sheet, or substituting the absorbent sheet for the base sheet itself. This device directs air upon the wetted absorbent sheet to cool this layer, and thereby conductively cool the patient's skin in thermal contact with the absorbent sheet. As one example, this device may be configured in serpentine shape, with multiple winding segments. The device may include body-contour slits extending inward from the perimeter, permitting the device to conform to a person's legs and outstretched arms. Cooling devices may also include optional features to enhance thermal contact between the absorbent sheet and the person's skin, and/or to prevent water runoff from the cooling field.

43 Claims, 15 Drawing Sheets

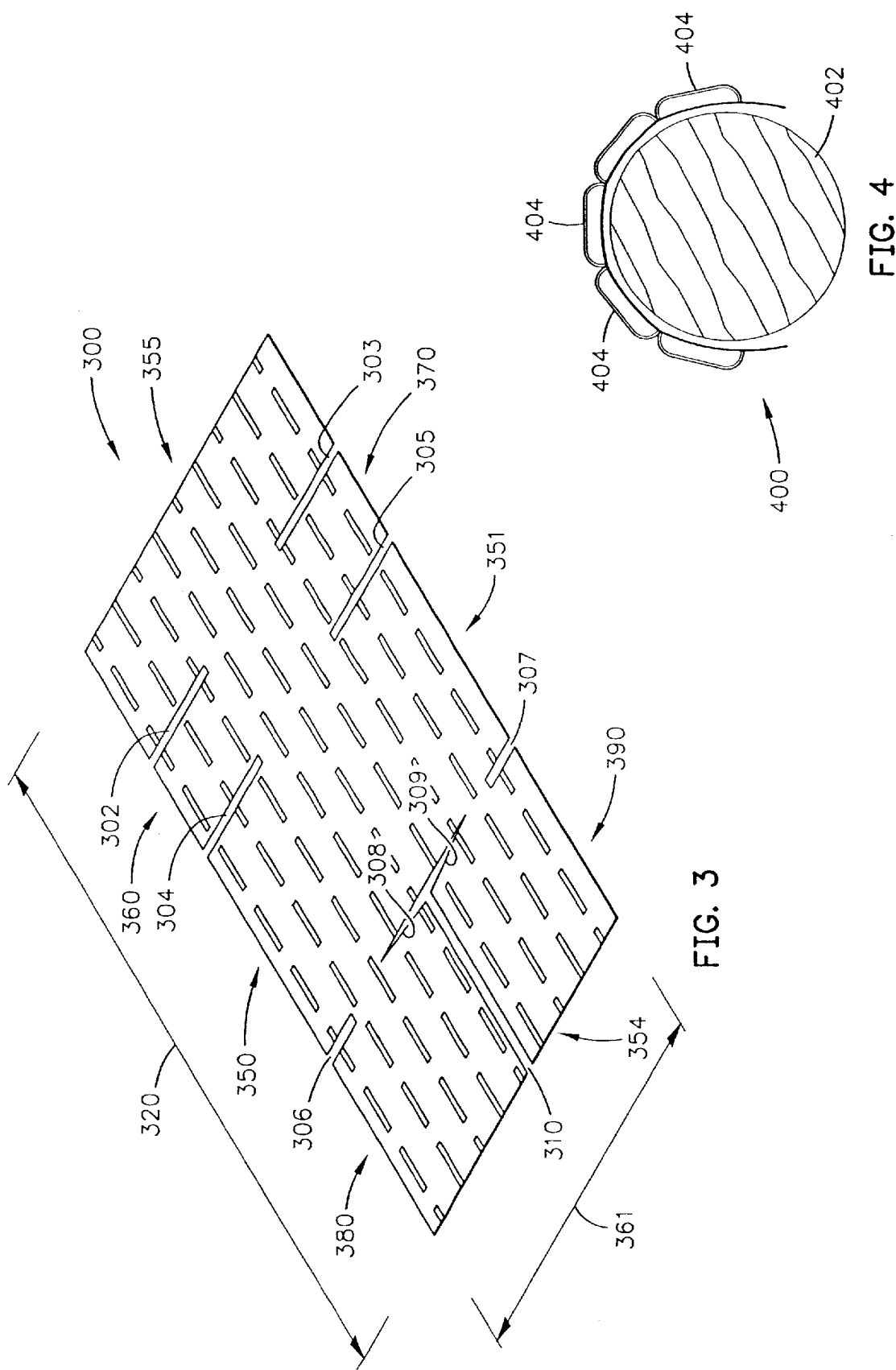

COOLING DEVICES WITH HIGH-EFFICIENCY COOLING FEATURES

CROSS REFERENCE TO RELATED APPLICATIONS

This application is a continuation of U.S. patent Application Ser. No. 10/016,934, filed Dec. 13, 2001 now U.S. Pat. No. 6,519,964, which is a divisional of U.S. patent application Ser. No. 09/546,513, filed Apr. 11, 2000, now U.S. Patent No. 6,354,099.

BACKGROUND OF THE INVENTION

1. Field of the Invention

The present invention relates to devices that utilize evaporative, convective, and/or conductive cooling to cool the human body in aid of surgery, medical treatment, therapy, or comfort. Some exemplary cooling structures include various configurations of thermal cooling devices.

2. Description of the Related Art

Temperature control in humans has important medical consequences. In order to maintain optimum health, the human body must maintain a core temperature within a very narrow range. Core body temperature changes as small as 0.1° Celsius trigger thermoregulatory responses such as vasoconstriction, vasodilation, shivering, or sweating. A narrow temperature range is optimal for human cellular functions, biochemical reactions, and enzymatic reactions. Outside this range of temperatures, the human body experiences hypothermia (excessive cold) or hyperthermia (excessive hot).

Hyperthermia can result from illness or environmental heat stress, among other causes. In some cases, healthy people suffer hyperthermia when their natural cooling mechanisms, such as sweating, are overwhelmed during heavy physical work in a hot environment. This situation can become even worse if the person fails to drink enough fluids, and therefore cannot sweat adequately. Heat stress disorders, categorized in ascending order of severity, include: heat cramps, heat syncope, heat exhaustion, and heat stroke. Normally, discomfort causes people choose to stop working before the onset of heat exhaustion, but competitive athletics or military activities sometimes push people beyond the limits of health.

Hyperthermia can also result from fever associated with illness. Fever may arise from infection, tumor necrosis, thyroid storm, malignant hyperthermia, brain injury, and other causes. Brain injuries that cause hyperthermia usually involve the hypothalamus, and may be caused by tumors, stroke, head injury, or cardiac arrest (in the case of ischemic brain injury).

Some consequences of hyperthermia include fluid and electrolyte imbalances, increased cellular metabolic rates, and cognitive impairment. More serious consequences include motor skill impairment, loss of consciousness, and seizures. Ultimately, hyperthermia can cause irreversible cellular injury (especially of the highly metabolic brain and liver cells), organ failure, and death. Hyperthermia is a condition that, depending on its severity, may require immediate cooling treatment to return the person's core temperature to normal.

Cooling treatment may also have other important uses. In some situations, mild or moderate hypothermia is believed to provide beneficial protection against injury. Moreover, induced hypothermia can be beneficial when the blood flow to some or all of the brain has been interrupted. Brain ischemia due to an interruption of blood flow may occur during cardiac arrest, surgery on the blood vessels of the brain, stroke, traumatic brain injury, or open heart surgery. Cooling the brain before (or in some cases after) these events can protect the brain from injury, or at least decrease the severity of the ultimate brain damage.

Physicians have used various devices and techniques to cool the human body, including pharmacological cooling and various types of mechanically induced cooling. Mechanically induced cooling approaches generally fall into one of these categories: conductive, convective, or evaporative. While different implementations have been tried, many are limited by lack of practicality, difficulty of use, ineffectiveness, and/or excessive power consumption.

One example of conductive cooling involves packing a hyperthermic person's body in ice, or immersing the person in cool or cold water. While ice is an effective cooling agent, it is painful to the person, potentially damaging to the skin, difficult to obtain in large quantities, and impractical for long term use. Water baths can be effective, although they are not practical for the comatose or intensive care patient, or for long term use. In one less effective, but common method of conductive cooling, a person may be placed in contact with a cold-water-circulating mattress and/or cover. Water inside the mattress removes heat from the person by conduction wherever the surface of the mattress thermally contacts the person's skin. Although there is some benefit to such devices, they are often uncomfortable and heavy, and provide inefficient thermal contact because they are not precisely shaped to the body.

In contrast to conductive cooling, convective cooling involves blowing air onto a person. Convective cooling is the least effective method of cooling from a thermodynamic point of view. Room temperature air can be blown very inexpensively with a fan. However, its cooling effectiveness is severely limited due to the thermal capacity of air, and related heat transfer coefficients.

For more efficient convective cooling, the air can be cooled before being blown onto the person. Air can be cooled, for example, with a traditional compression or heat-pump air conditioner, vortex cooling, or with thermo-electric cooling. Cooled air can also be generated using the "swamp cooler" principle of vaporizing water into the air stream. When water evaporates into the air, it cools the air. Then, the cooled air is applied to a person.

After the air is cooled with one of the foregoing techniques, it can be delivered to a person by cooling the air in the person's room. To save energy, cooling can be confined to the person rather than the whole environment surrounding the person. One technique that uses this approach is the convective thermal device, which has been implemented in a variety of forms.

Although convective cooling removes the stress of environmental heat, it is minimally effective in active cooling. This limited thermodynamic effectiveness is particularly evident when trying to cool people with fevers. Generally, in order to be cooled by convection, a feverish person must be anesthetized and paralyzed to prevent the body's heat-producing shivering response. Further, due to the thermodynamic inefficiency of convective cooling, this method of cooling uses considerable electrical power and generates considerable waste heat, which can be a problem in emergency rooms or intensive care units.

Having discussed conductive and convective cooling, the final mechanically induced cooling mechanism is evaporative cooling. Sweating is a principal example of evaporative cooling. Because water has a large heat of vaporization, large amounts of heat can be removed from the body by evaporating relatively small amounts of water. For example, when a gram of water evaporates, it extracts 540 calories of heat (2.26 kJ) from the skin. On hot summer days, many people practice basic evaporative cooling by wetting their skin or clothing with water, and permitting the water evaporate. Medical staff employ evaporative cooling by giving sponge baths to patients, where the unclothed patient is wetted with water and allowed to dry by evaporation. Sometimes a fan is pointed at the person to increase the evaporation rate. While sponge baths are indeed effective, they are labor intensive, messy, demeaning to body-conscious people, and impractical for prolonged cooling. Finally, evaporative cooing has limited effectiveness in high humidity environments Therefore, as shown above, conductive, convective, and evaporative cooling systems each have certain benefits and limitations. And, although some of the foregoing cooling products have certain advantages and might even enjoy some commercial success, engineers at Augustine Medical, Inc. are continually seeking to improve the performance and efficiency of human cooling systems. Some areas of possible focus include simplifying hardware designs, boosting the effectiveness of cooling systems, and cooling specific body parts.

An additional area of focus concerns the management of the liquid source during evaporative cooling. Introducing too much liquid causes liquid to spill over the area of focused cooling (the "cooling field"), and pool under the person. Pooling of contaminated liquids presents hygienic and esthetic problems in the medical environment. On the other hand, if too little liquid is supplied, the cooling field may dry out and stop or reduce cooling effectiveness.

SUMMARY OF THE INVENTION

Broadly, the present invention introduces cooling devices that utilize evaporative, convective, and/or conductive cooling to reduce a person's temperature in aid of surgery, medical treatment, therapy, or comfort.

One improved cooling device maximizes evaporative cooling by aiding the flow of air to the body and also removing vapor-laden air from the body. This device includes an upper sheet and a base sheet adhered in many locations such that the sheets cooperatively form an inflatable structure. The inflatable structure includes numerous elongated, substantially parallel, inflatable cooling chambers, and between each pair of neighboring cooling chambers, a connecting membrane. The inflatable structure also includes numerous ventilating cross-members, each of which spans and interconnects the cooling chambers. Air enters the chambers through an air inlet in the inflatable structure, and then exits the chambers toward the person through numerous exhaust holes located in the base sheet. After being heated by the person's body, this air can exit the inflatable structure through evaporation openings in the connecting membranes.

In a different embodiment, upper and base sheets may be adhered in different locations to provide a cooling device with a cooling chamber that forms a continuous a serpentine path. The serpentine cooling chamber is held in this configuration by connecting membranes between neighboring segments of the path. In this embodiment, ventilating cross-members are unnecessary because all regions of the cooling chamber are in fluid communication with each other. After air enters the chamber through an air inlet in the structure, the air exits the chamber toward the person through numerous exhaust holes located in the base sheet. After being heated by the person's body, this air can exit the inflatable structure through evaporation openings defined in the connecting membranes.

Another embodiment of the invention concerns a generally rectangular cooling device that includes certain body-conforming features. Namely, the device has a number of body-contour slits extending inward from the perimeter. Due to the slits' locations, they permit the inflatable structure to conform to a person's legs and outstretched arms.

Still another embodiment of the invention concerns an inflatable cooling device that includes an evaporative cooling layer. This layer comprises a sheet of absorbent material capable of holding a substantial amount of water. The absorbent sheet is placed in thermal contact with the person's skin, saturated with water, and then evaporatively cooled by the overlying thermal cooling device. As this layer cools (by evaporation), it has the effect of cooling the person (by conduction). The absorbent sheet may advantageously comprise a super-absorbent material such as starch-grafted sodium polyacrylate.

Accordingly, as discussed above, the invention may be implemented to provide various types of apparatus, such as cooling devices described herein. In contrast, certain other embodiments concern methods for utilizing such apparatuses.

The invention affords its users with a number of distinct advantages. By using a blower to induce evaporative cooling, the invention avoids the need for power consuming refrigeration equipment. As another advantage, evaporative cooling is thermally self-limiting, because it will not produce surface temperatures that would freeze skin, as is the case with ice packs. Also, unlike ice and other phase change materials that can only maintain fixed temperatures for a limited time, cooling with this invention can be sustained indefinitely by periodically adding water to the cooling field.

As another advantage, absent from previous approaches, this invention may incorporate a super-absorbent material into cooling devices. The super-absorbent material is capable of holding a large volume of water relative to its mass. This material, once wetted, can provide hours of evaporative cooling without the need for a liquid reservoir and piping system to replenish the cooling field. Consequently, cooling devices of this invention help discourage the introduction of too much cooling liquid, and help prevent the cooling liquid from overwhelming the cooling field and spilling over.

Furthermore, the cooling devices of this invention include improved means to direct air flow through the device, maximizing delivery of dry air to all areas of the cooling field. Additionally, the invention employs ventilation openings to aid the escape of saturated vapor from the cooling field and allow an increased influx of dry air. The invention also provides a number of other advantages and benefits, which should be apparent from the following description of the invention.

BRIEF DESCRIPTION OF THE DRAWINGS

FIG. 3 is a perspective view of an inflatable cooling device having a number of body-contour slits, according to the invention.

FIG. 4 is a cross-sectional side view showing how body-contour slits permit a section of inflatable cooling device to conform to a limb, according to the invention.

DETAILED DESCRIPTION

The nature, objectives, and advantages of the invention will become more apparent to those skilled in the art after considering the following detailed description in connection with the accompanying drawings.

HARDWARE COMPONENTS & INTERCONNECTIONS

Introduction

One aspect of the invention concerns a cooling device, implemented in various forms of cooling device as discussed below. This equipment is used to cool the human body in aid of surgery, medical treatment, therapy, or comfort. The invention utilizes evaporative, convective, and/or conductive cooling. With evaporative cooling, a cooling liquid is applied to bodily regions, and then an evaporating gas is blown upon those regions to encourage evaporation of the cooling liquid, thereby cooling the body. Convective cooling occurs when cool air is blown upon a relatively warm body, independent of any evaporative activity. With conductive cooling, the cooling structure itself is directly cooled, and since the cooling structure contacts the person, the person is ultimately cooled as well.

General Structure

Cooling devices of this invention may take various forms as discussed below; they are generally flexible coverings that lie on and drape over a body. After draping such a cooling device over a person's body, an operator configures the device to blow air onto the person and thereby cool the person by convection, evaporation, and/or conduction. The inlet air may be dehumidified in advance, to increase its water-carrying capability and resultant cooling ability.

Figure 1:
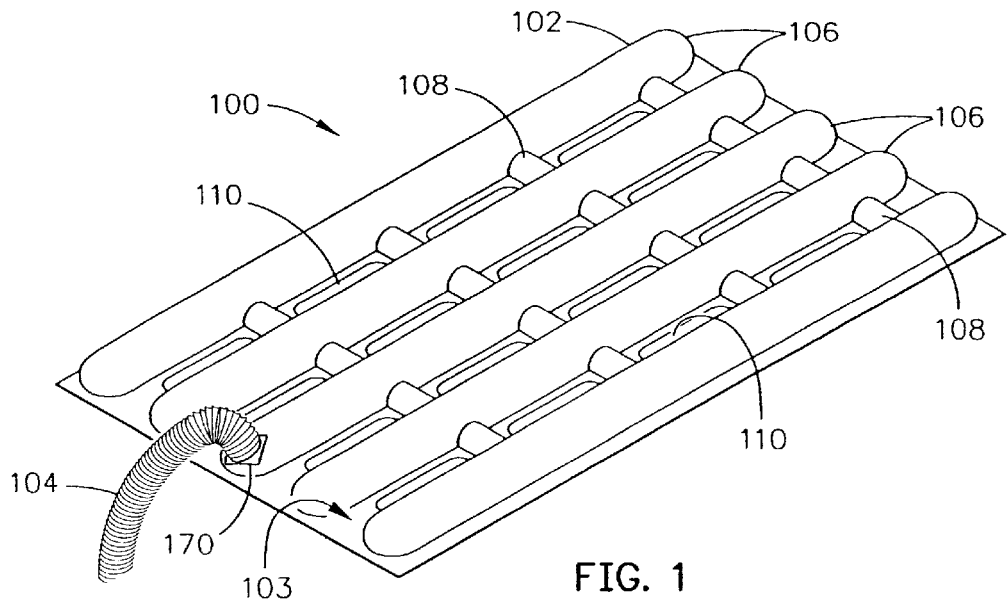
FIG. 1 is a perspective view of an improved inflatable cooling device according to the invention.

FIG. 1 depicts one example, as shown by the device 100. The device 100 is constructed from upper and lower sheets that are adhered together in various locations, such that the sheets cooperatively form an inflatable structure. This inflatable structure includes numerous elongated, substantially parallel inflatable cooling chambers 106. Between each pair of neighboring cooling chambers 106 is a connecting membrane, exemplified by the connecting membrane 103. As an example, the connecting membranes 103 may comprise substantially flat regions where the upper and lower sheets are bonded, and serve to provide space between neighboring cooling chambers 106. Also located between each pair of neighboring cooling chambers 106 are numerous ventilating cross-members, such as the cross-member 108. The cross-members permit air to flow freely between the cooling chambers 106 despite the inter-chamber gap introduced by the connecting membranes 103. The device 100 also includes an inlet 170, which may be permanently or removably attached to an inlet hose 104.

In the connecting membranes between adjacent cooling chambers, there are multiple evaporation openings 110, each penetrating both sheets. The separation of the cooling chambers 106, made possible by the connecting membranes 103 and cross-members 108, facilitates the presence of these evaporation openings. The evaporation openings 110 may comprise relatively large openings (as shown), patterns or other groups of many smaller openings, or natural openings in porous, fibrous, or otherwise air permeable materials.

Figure 2:
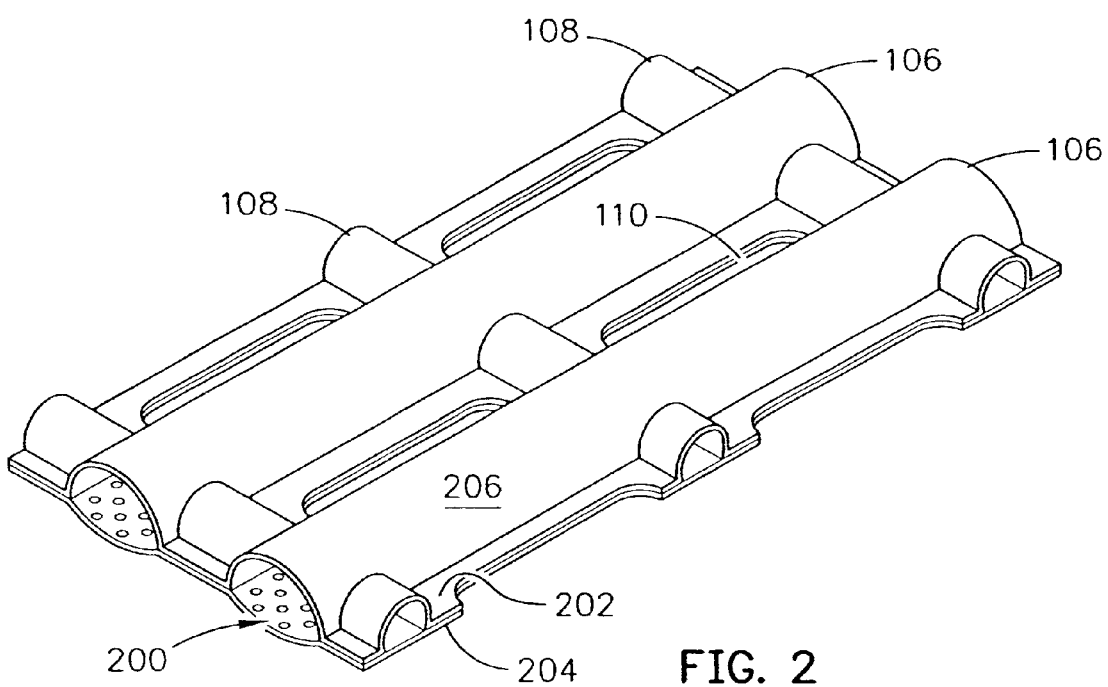
FIG. 2 is a partial, cutaway perspective view of the inflatable cooling device of FIG. 1.

FIG. 2 shows additional features of the cooling device in more detail. Referring to FIG. 2, the upper sheet 202 and the base sheet 204 are individually shown. In regions of the base sheet 204 that define the cooling chambers 106, there are numerous exhaust holes. As an example, the base sheet 204 defines numerous exhaust holes 200 in the regions of the base sheet 204 that form the chamber 206. In one embodiment, the base sheet 204 may comprise an otherwise air impermeable material, with many tiny holes 200 defined therein. In another embodiment, the base sheet 204 may include an air permeable exhaust region made from a substance such as a woven fabric, mesh, a flexible lattice, fibrous structure, or another substance that naturally defines many tiny holes 200. Additional apertures may be created to enhance airflow if desired.

Different Chamber Configurations

Serpentine: One Example

Figure 1A:
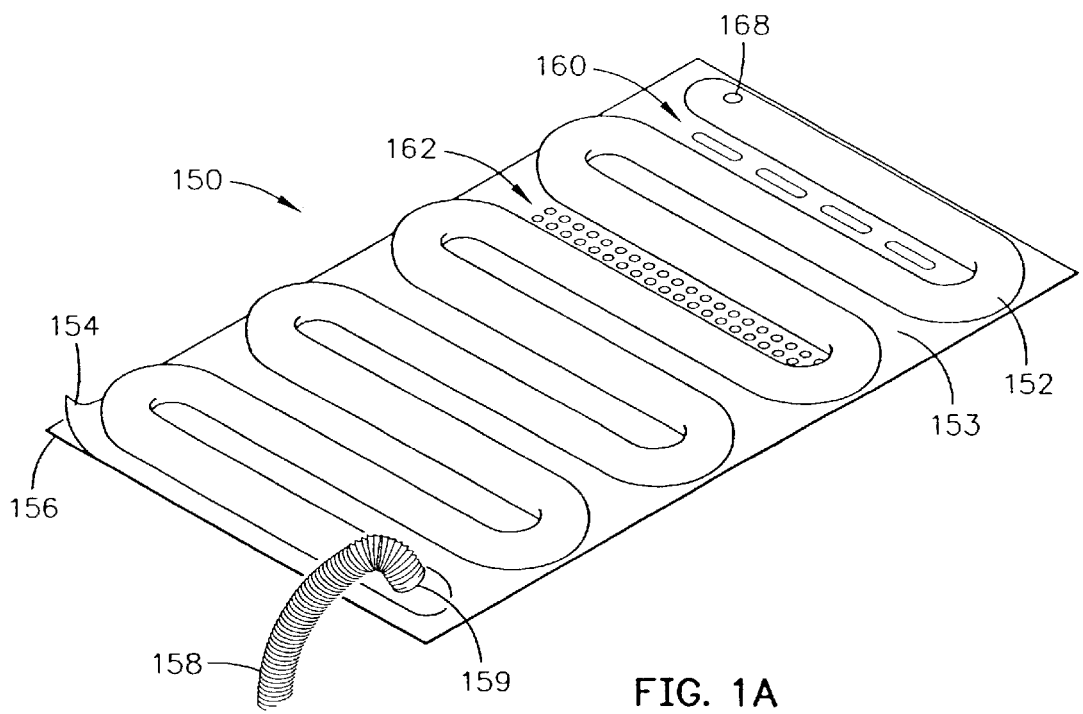
FIG. 1A is a perspective view of an inflatable cooling device with a different chamber configuration according to the invention.

FIG. 1A shows a different construction of cooling device, with one a cooling chamber that forms a continuous a serpentine path. The device 150 includes upper and base sheets 154, 156, which are separated at one corner of the device for illustration purposes only. The sheets 154, 156 are adhered in various locations, such that the sheets cooperatively form an inflatable structure. As depicted, this inflatable structure includes a single serpentine cooling chamber 152. Neighboring segments of the chamber 152 are separated a region of the upper/base sheets referred to as a connecting membrane, exemplified by the connecting membrane 153. As an example, the connecting membrane may comprise substantially flat regions where the upper and lower sheets are bonded, and serve to provide space between neighboring segments of the serpentine chambers 152.

Ventilating cross-members (such as 108 in FIG. 1) may be utilized, although they are unnecessary due to the contiguous nature of the serpentine chamber 152. Namely, air freely flows throughout the contiguous, one-piece chamber 152.

In the connecting membrane between adjacent paths of the chamber 152, there are multiple evaporation openings, each penetrating both sheets. The evaporation openings may comprise relatively large openings 160, patterns or other groups of smaller openings 162, or natural openings (not shown) in porous, fibrous, or otherwise air permeable materials.

The base sheet 156 may comprise similar materials as in the previously illustrated device 100, wherein the base sheet includes multiple exhaust holes (not shown) in regions that constitute the chamber 152. Air enters the chamber through an inlet 159, which may be permanently or removably attached to an inlet hose 158. Air enters the chamber 152 via the inlet 159, and ultimately exits the chamber toward the person through the exhaust holes located in the base sheet. An exit port 168 may be added to moderate inflation pressures. After being heated by the person's body, this air can exit the inflatable structure through evaporation openings 160, 162 defined in the connecting membranes.

Different Serpentine Chamber Configurations

Figure 1B:
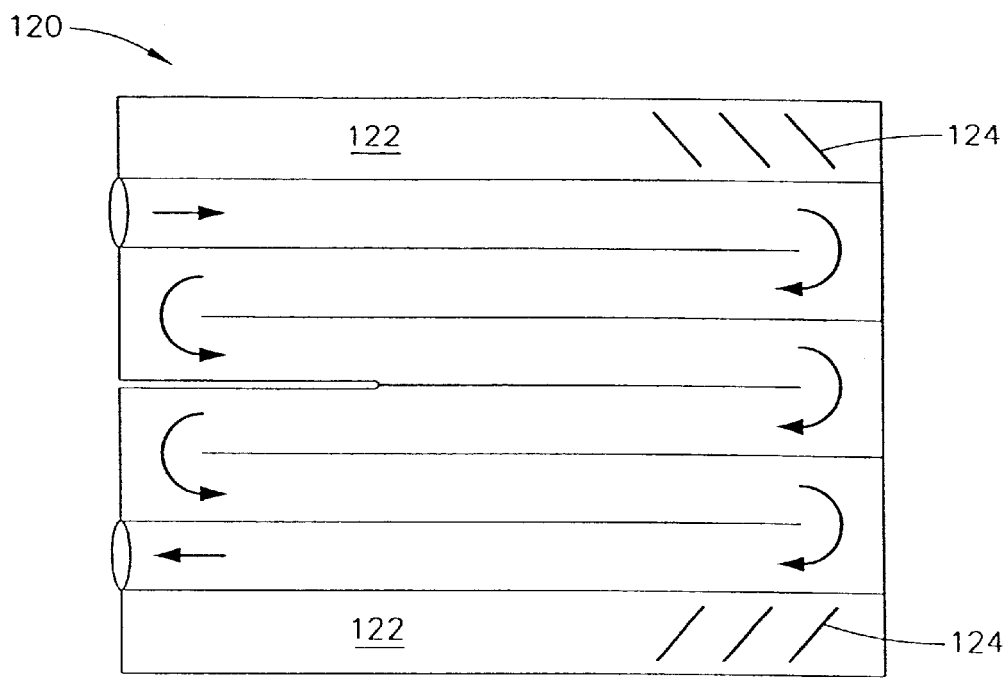
FIGS. 1B–1F are plan views of various inflatable cooling devices with different chamber configurations according to the invention.
Figure 1C:
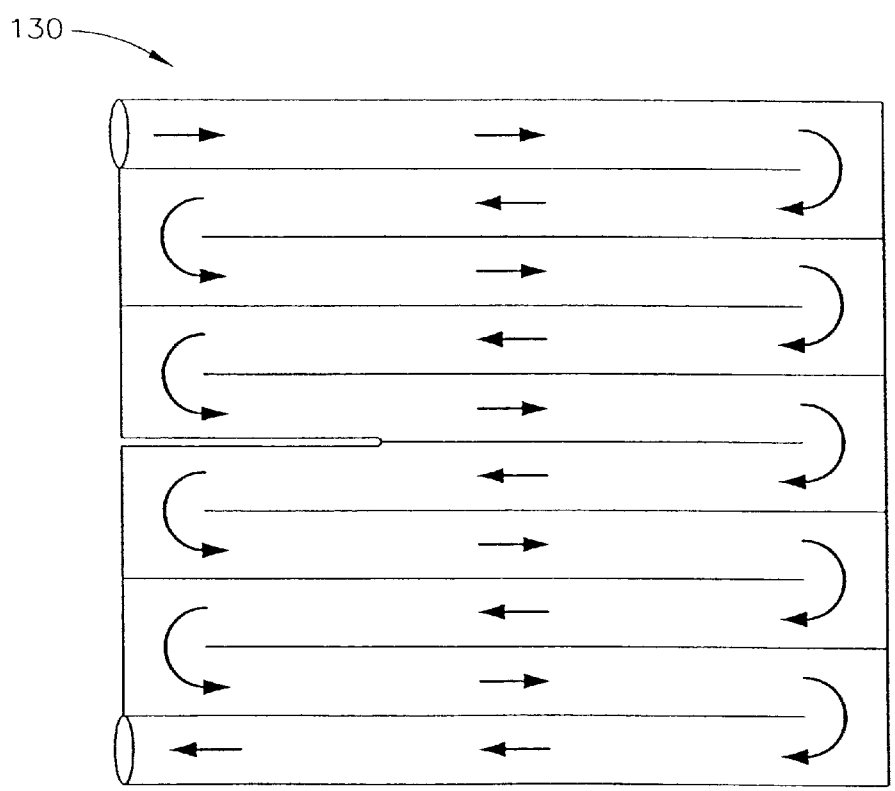

In addition to the serpentine pattern specifically illustrated in FIG. 1A, the invention contemplates a variety of other serpentine patterns. For example, FIG. 1B illustrates a cooling device employing a contiguous serpentine chamber having six parallel segments. The device 120 also includes drapes 122 and slits 124, for use as described below. As a different example, FIG. 1C exemplifies a cooling device 130 with a contiguous serpentine chamber having ten parallel chambers.

Figure 1D:
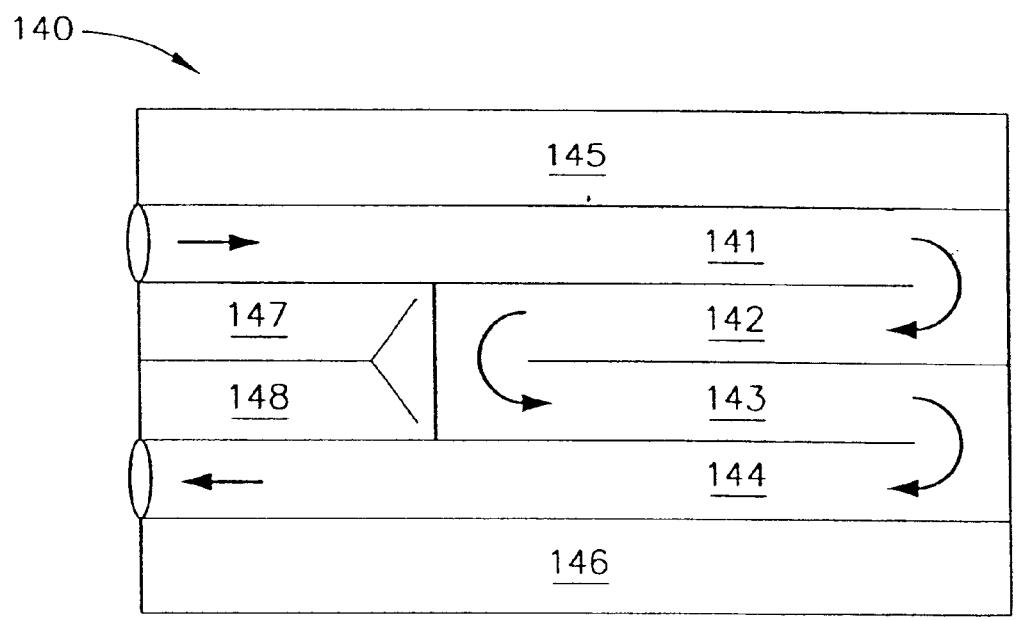

FIG. 1D depicts a cooling device 140 with a four-segment serpentine chamber, including two longer segments 141, 144 and two shorter segments 142–143. With this configuration, the device end with the shorter chambers 142–143 is placed over the patient's torso. For reasons described below, the device 140 may include drapes 145–148.

Figure 1E:
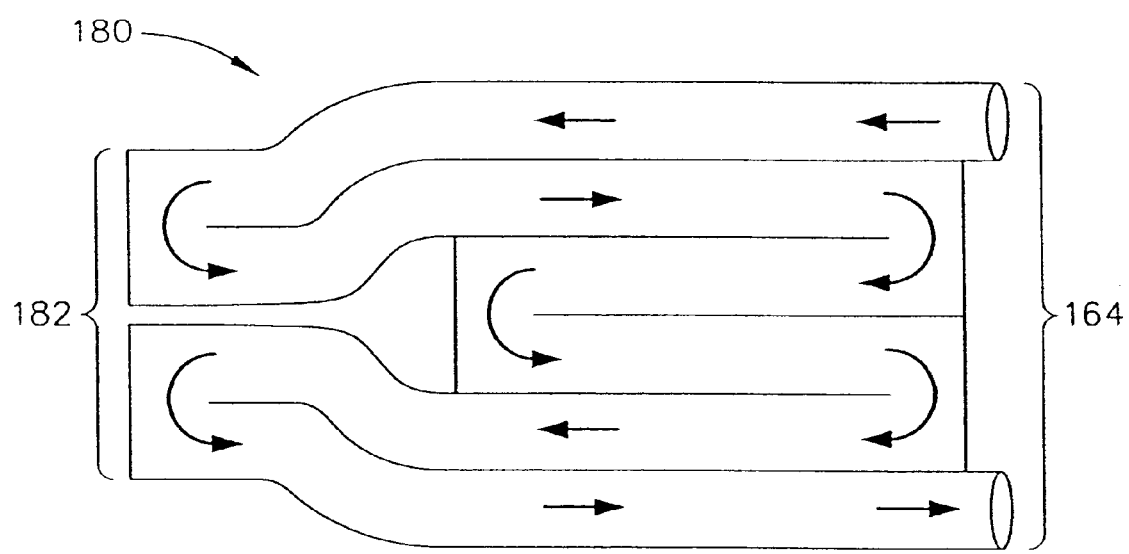
Figure 1F:
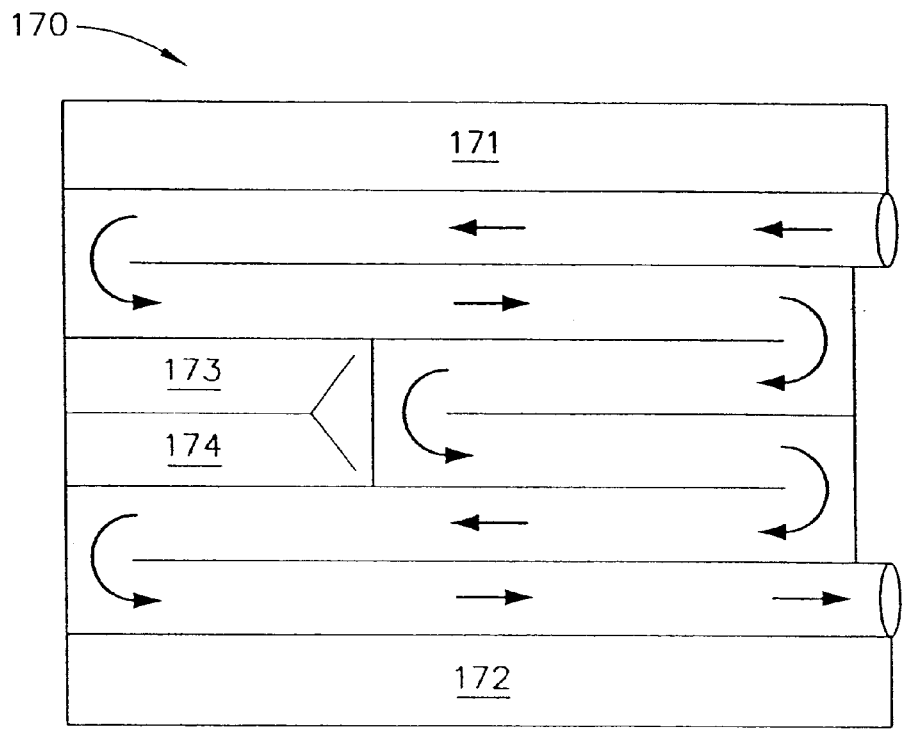

FIG. 1E depicts a device 180 having a contiguous serpentine chamber including six segments configured as shown. With this arrangement, the device's narrower end 182 may be oriented toward the patient's feet with the wider end 164 toward the patient's head. FIG. 1F shows still another cooling device 170, with a serpentine chamber that includes six segments configured as depicted. The device 170 includes drapes 171–174, the functions of which are described below.

In addition to the foregoing patterns, the invention also includes a variety of other shapes that provide similarly enhanced airflow. For example, the device may include one or more chambers exhibiting a grid pattern, crisscrossing pattern, lattice, intersecting circles, etc.

Body-Conforming Shape

The present invention contemplates various modifications enabling cooling devices to more closely conform to the human shape. To illustrate one example, FIG. 3 depicts a cooling device 300 with a generally rectangular outline that defines sides 350–351, a bottom edge 354, and a top edge 355. The device 300 has a longitudinal dimension 320 and a lateral dimension 361.

The device 300 readily conforms to the human shape because of various body-contour "slits" extending inward from the device's perimeter. Although illustrated by cuts or breaks in the device, slits may also be embodied by perforated areas, weakened regions, loosely bound areas, or other intended patterns of weakness. Furthermore, slits may include sealed seams where needed to prevent deflation of inflatable components. The slits are advantageously located so as to permit the device 300 to conform to a supine person's legs and outstretched arms. Although the exact position of each slit may be varied while still achieving the goal of conforming the device 300 to the person's limbs, FIG. 3 shows one exemplary configuration of slits 302–310.

The slits 302–305 define a arm pair of complementary arm flaps 360, 370, which longitudinally bend about the person's outstretched arms (not shown). The slits 306–309 are aligned with the person's hips, with the slit 310 being running parallel (and in between) the person's legs. The slits 306, 308, 310 define one leg flap 380, which can laterally bend about the curvature of the person's right leg (not shown). Similarly, the slits 307, 309, 310 define another leg flap 390, which can laterally bend around the curvature of the person's left leg (not shown).

Additional slits (not shown) may be defined to permit the device to further conform to other bodily features (e.g., head, neck, or joint), to persons in non-supine positions (e.g., lying on a side). The locations for such slits will be apparent to ordinarily skilled artisans, having the benefit of this disclosure.

FIG. 4 shows how an exemplary section 400 of cooling device conforms to a person's leg 402. The device section includes cooling chambers 404, which wrap around the person's leg 402 as shown.

Ordinarily skilled artisans (having the benefit of this disclosure) will also recognize that, in addition to the particularly illustrated device 100, the body-conforming features discussed above may be applied to other inflatable cooling devices, non-inflatable device, or other layers of body covering.

Thermal Device With Absorbent Sheet

Introduction

As an enhancement to cooling devices, the present invention introduces an absorbent layer attached to a cooling device or merely placed beneath the cooling device. This absorbent layer, also called an "absorbent sheet," comprises a material that readily absorbs water. This enhanced device design operates by evaporatively cooling the water-filed absorbent sheet. While the absorbent sheet thermally contacts the person's skin, cooling of the absorbent sheet (by evaporation) has the effect of cooling the person's skin (by conduction).

Addition of Absorbent Sheet: Basics

Figure 5:
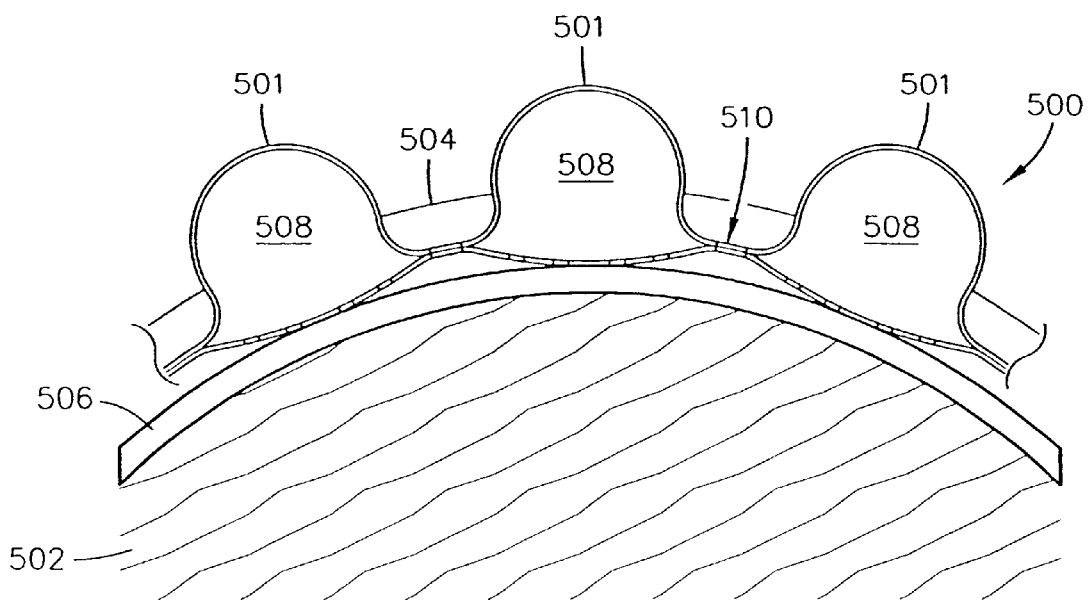
FIG. 5 is a partial cross-sectional side view showing an inflatable cooling device of the invention draped over a person, where the device is equipped with an absorbent sheet according to the invention.

The absorbent sheet may be utilized with a variety of different inflatable cooling devices, such as the embodiment of FIGS. 1–3, the devices shown in the commonly assigned U.S. Pat. No. 5,860,292, or still different embodiments. For ease of explanation, the absorbent sheet is introduced in the context of a device constructed according to FIGS. 1–2, since this embodiment has already been described in some detail. FIG. 5 shows an inflatable cooling device 500 in partial cross-section, including three cooling chambers 501. When inflated, each cooling chamber 501 includes an interior region 508 filled with air. Neighboring chambers are interconnected by connecting membranes (such as 510) and ventilating cross-members (such as 504).

In use, the device 500 is draped over a person's body 502. Between the device 500 and the person lies an absorbent sheet 506. For ease of use, the layer 506 may be permanently attached to the device 500, or removably attached by clips, hook-and-loop fasteners, snaps, ties, etc. For even greater flexibility, the layer 506 may be completely separate from the device 500, with no interconnection whatsoever.

The absorbent sheet 506 comprises a layer of material that readily absorbs water and is amenable to evaporative cooling under air flow caused by the overlying device 500. As one example, the layer 506 may comprise a substance capable of absorbing significantly more water than its own mass and volume. These materials are known as "superabsorbent," and one example is starch-grafted sodium polyacrylate (SAP), which is present in some types of diapers. SAP material may be processed into a fibrous, cotton-like form and woven into a sheet of gauze-like material.

SAP material can absorb more than twice its volume and four hundred times its mass in water. Thirty grams of SAP (less than the amount in a typical disposable diaper) can absorb approximately 1,000 grams of water. The evaporation of 1,000 grams of water removes 2,400 kilojoules of heat. If a typical seventy kilogram human has a specific heat near the specific heat of water, it would only take 1470 kilojoules to reduce the mean body temperature by five degrees Celsius. Thus, as discovered by the present inventor (s), and illustrated by the foregoing example, water held by a super-absorbent sheet can provide a significant amount of cooling. The duration of cooling is significant, as well. Namely, while sleeping, the body metabolically generates about one hundred Watts of heat. This heat generation would be canceled by the evaporation of about 1,000 grams of water per hour, neglecting thermal losses in the system. At this rate, one liter of water would provide about six hours of cooling.

Absorbent sheet With Boundary Layers

Figure 6:
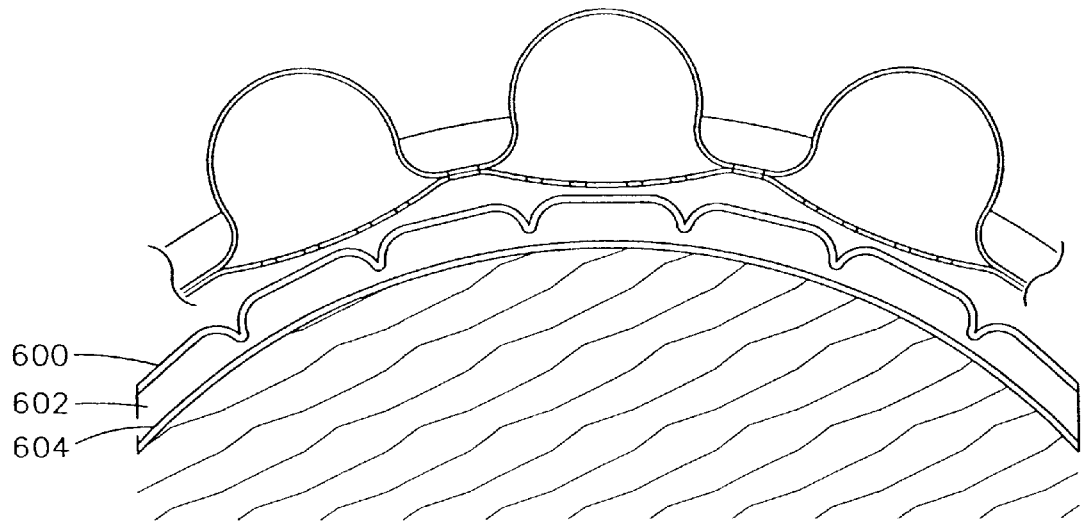
FIG. 6 is a partial cross-sectional side view showing an inflatable cooling device of the invention draped over a person, where the device is equipped with a different embodiment of absorbent sheet according to the invention.

FIG. 6 shows a different configuration of cooling device incorporating an absorbent sheet. The device components and attachment (or lack of attachment) to the absorbent sheet are similar to FIG. 5. However, in this example the absorbent sheet 602 is sandwiched between boundary layers 600, 604, which add properties that may be absent from the absorbent sheet, such as strength, comfort to the skin, etc. The boundary layers 600, 604 may be woven or non-woven. Although the upper boundary layer 600 must be liquid permeable to permit water passage to/from the absorbent sheet 602, the lower boundary layer may comprise plastic or another water impermeable substance that keeps the person dry.

The layers 600–604 may comprise parallel layers that are stitched, clipped, or otherwise held together to form a quilt-like structure. Alternatively, the layers 600, 604 may be stitched or otherwise bonded together to define pockets that contain isolated patches of absorbent material 602. The absorbent material should loosely fill such pockets to allow for swelling as water is absorbed, and avoid forming rounded bunches of material that only tangentially contact the person.

Integrated Absorbent Sheet

Introduction

In contrast to the embodiments shown above in FIGS. 1–2 and 4–5, a different embodiment of the invention omits the base sheet as discussed above, and utilizes an absorbent sheet as the base sheet instead. This embodiment is said to use an "integrated" absorbent sheet. This device includes an upper sheet attached to an absorbent sheet at various places to form one or more inflatable cooling chambers, of desired shape and number. In regions where the upper sheet and absorbent sheet are not adhered, these materials can separate when air flows between them, thereby defining the inflatable cooling chambers. Regions where the upper sheet and absorbent sheet are joined form connecting membranes located between the chambers.

Previously described embodiments (e.g., FIGS. 5–6) cool the absorbent sheet by directing air through holes in the base sheet onto the absorbent sheet. In contrast, the present embodiment utilizes the existing circulation of air through the cooling chambers to cool the absorbent sheet. This is now possible because the absorbent sheet actually forms the bottom of the cooling chambers. The absorbent sheet may also be called an evaporative cooling sheet or layer. Moisture-laden air from the evaporative cooling layer can be released in various ways, as shown below.

Releasing Moist Air

Figure 7:
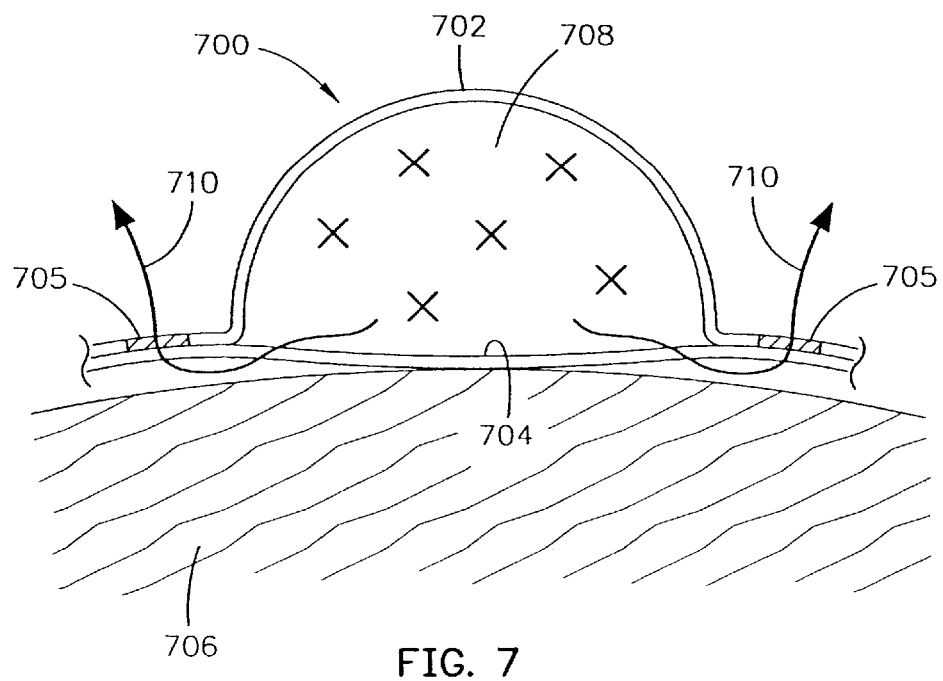
FIG. 7 is a cross-sectional side view of an inflatable cooling chamber with absorbent base sheet, according to the invention.
Figure 8:
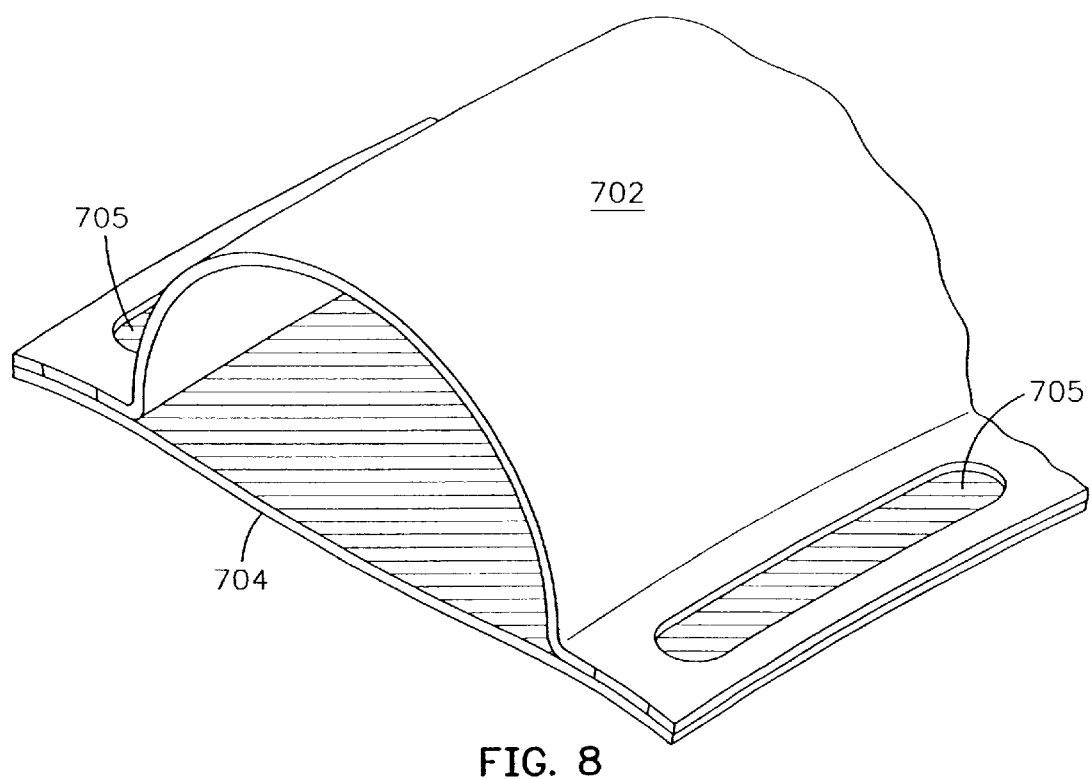
FIG. 8 is a cutaway perspective view of the inflatable cooling chamber of FIG. 7.

As one example, the moisture-laden air from the evaporative cooling layer may be released through evaporation openings or "vents." FIGS. 7–8 cross-sectionally depict a cooling chamber 700 and various subcomponents including a an upper sheet 702, base sheet 704, evaporation openings 705, and interior region 708 of air space inside the inflatable chamber 700. As shown, the chamber 700 is placed atop a person's body 706. The base sheet 704 is provided by an evaporative cooling layer, comprising gauze, woven material, non-woven porous, or other water absorbent sheet.

The evaporation openings are defined in connecting membranes next to cooling chambers, such as the chamber 700. Since the base sheet 704 is naturally air permeable, creation of the evaporation openings is achieved by forming air permeable regions in the upper sheet 702. The evaporation openings may comprise relatively large openings (as shown), patterns or other groups of smaller openings, or a region of porous, fibrous, or otherwise air permeable material.

The chamber 700 is inflated by directing air into the region 708 between the sheets 702, 704. This air encourages the base sheet 704 to evaporate water, and thereby reduce its temperature. Moisture-laden air can escape from the chamber 708 by traveling through the base sheet 704 and then out the evaporation openings 705, into the ambient air. As an additional feature, the upper sheet 702 may include one or more see-through regions, enabling an operator to visually monitor wetness of the absorbent sheet 704.

Figure 13A:
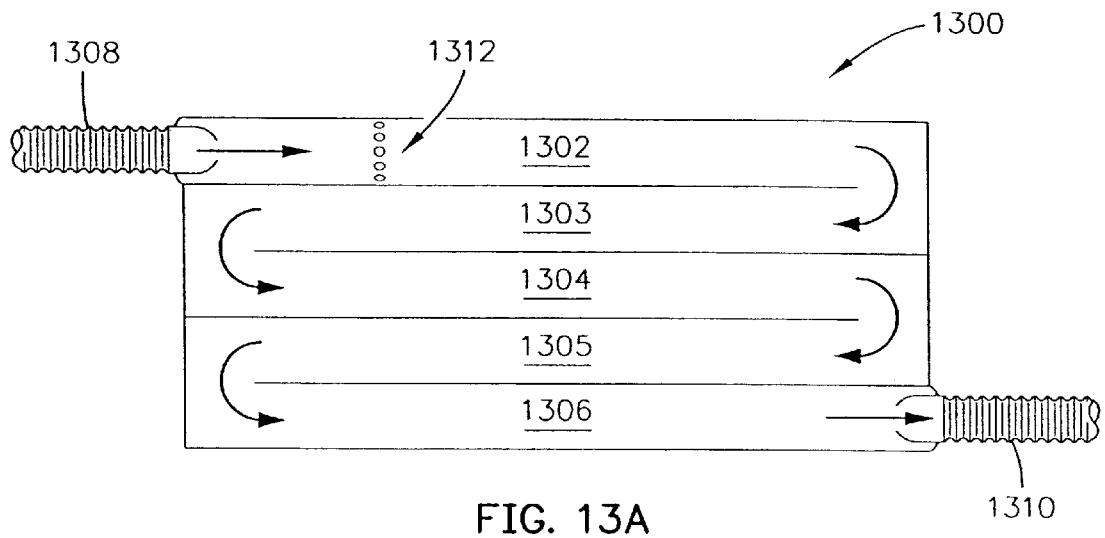
FIG. 13A is a perspective view of a cooling device with a continuous path serpentine cooling chamber, according to the invention.

FIGS. 13A shows a different option for evacuating moisture laden air from cooling chambers. As shown below, this embodiment is especially effective with a one-piece, serpentine cooling chamber. Briefly, moist air escapes the cooling chambers through evaporation openings 1312 defined in the upper sheet.

Figure 13B:
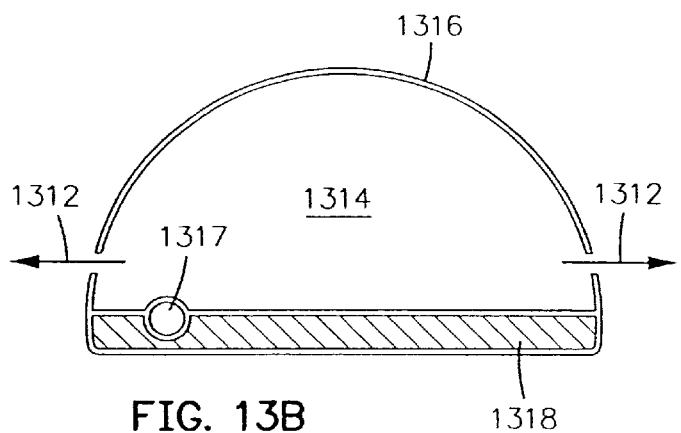
FIG. 13B is a cross-sectional side view of one cooling chamber of the cooling device of FIG. 13A in greater detail.

FIG. 13A shows a cooling device 1300 with multiple cooling chambers 1302–1306 cooperatively forming a one-piece, serpentine cooling chamber. Air travels through the chambers 1302–1306 in a single direction because it fills the chambers 1302–1306 at an inlet 1308, and exits at an outlet 1310. As shown more clearly in FIG. 13B, each chamber is defined by an upper sheet 1316 and an absorbent base sheet 1318 that comprises an evaporative cooling sheet such as a super-absorbent sheet. Air from the interior space region 1314 of each chamber escapes through the evaporation openings 1312. Optionally, the absorbent base sheet may include a liquid delivery tube 1317 to replenish evaporated fluids.

Advantageously, the device 1300 produces substantial evaporation, and therefore substantial cooling. This is because the device 1300 maintains substantial air flow throughout the path from inlet 1308 to outlet 1310, and evaporation is greatly affected by the air flow volume. Evaporation by the device 1300 is also enhanced by the location of the evaporation openings 1312. Namely, as the air stream picks up moisture, a concentrated boundary layer forms, with the most humid air residing just above the wetted surface. That is boundary layer restricts drier, upper level air from reaching the wetted surface. Thus, the openings 1312 placed near the seam between the base sheet 1318 and the upper sheet 1316 effectively vent air out from the wet boundary layer. This shrinks the boundary layer's thickness and allows the dry air to more effectively pick up moisture.

Structure to Enhance Device-Person Thermal Contact

In devices with integrated absorbent sheets, effective cooling requires good thermal contact between the evaporative cooling layer and the patient's skin. Accordingly, the present invention includes a number of features designed to enhance thermal contact between the absorbent base sheet and the patient's skin. The weight of the thermal device is one feature that encourages thermal contact. In addition to its own mass, weights, cotton blankets, or any other ballast may be placed over the device to make the device heavier and improve thermal contact.

Figure 9A:
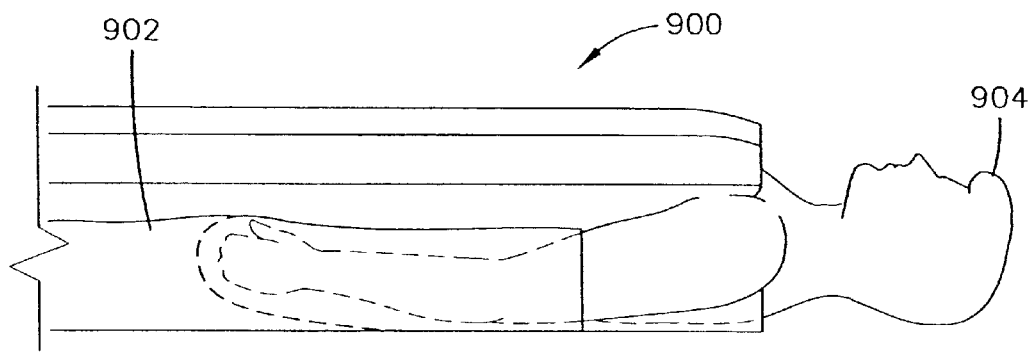
FIG. 9A is a side view of a cooling device with hand pockets, according to the invention, where the device is placed over a person.
Figure 9B:
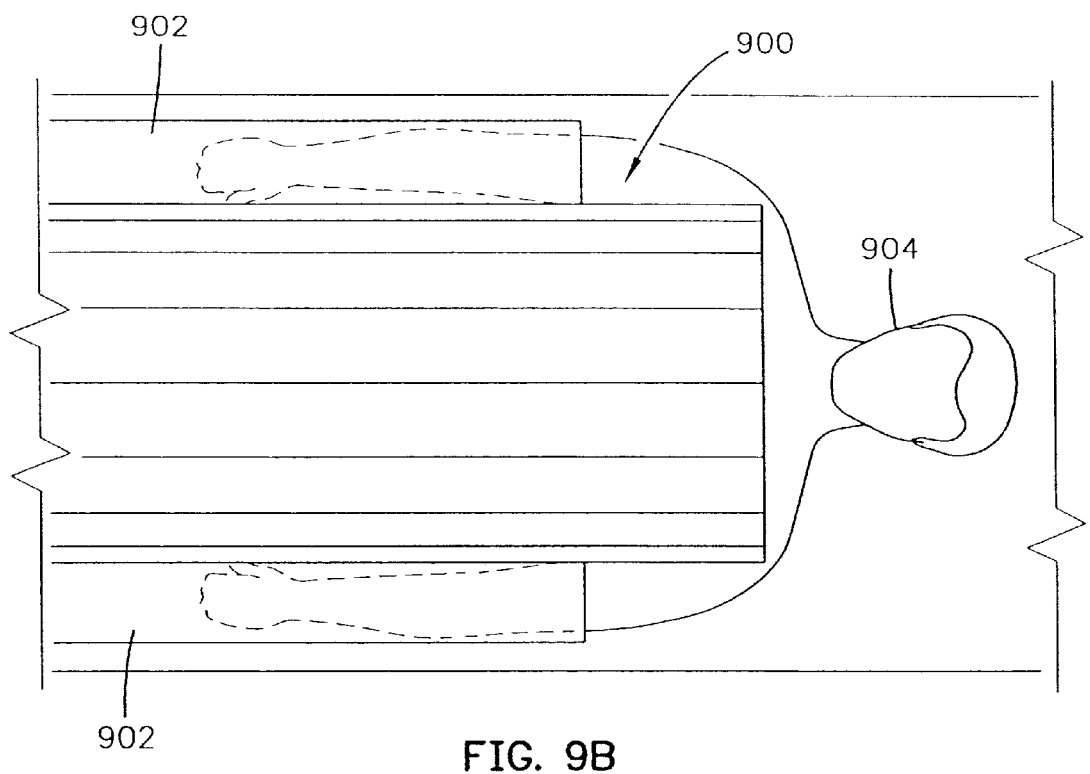
FIG. 9B is a top view of the cooling device of FIG. 9A, where the device is placed over a person.

Hand pockets are another feature to enhance thermal contact between the absorbent sheet and the patient. FIGS. 9A–9B depict a cooling device 900 placed over a person 904. On opposite sides of the device 900, hand pockets 902 are formed. When the person 904 places his/her hands inside the hand pockets 902, this holds the device 900 down against the person's torso, thereby encouraging thermal contact between the person and device. Each hand pocket may be implemented in by various different structures attached to the device, such as hand-receiving tubes, z-folded device fabric, cuffs, sleeves, etc.

Body drapes are still another feature to enhance thermal contact between the absorbent sheet and the patient. A number of body drapes have been introduced in FIGS. 1B, 1D, and 1F. Broadly, body drapes are regions of the device that can be tucked under the patient to hold the device against the patient's skin. As one example, the body drapes may comprise predefined, flattened, non-inflatable regions or other suitable structure for tucking beneath the patient. Body drapes may be placed in various locations to provide torso drapes, leg drapes, etc.

Figure 10:
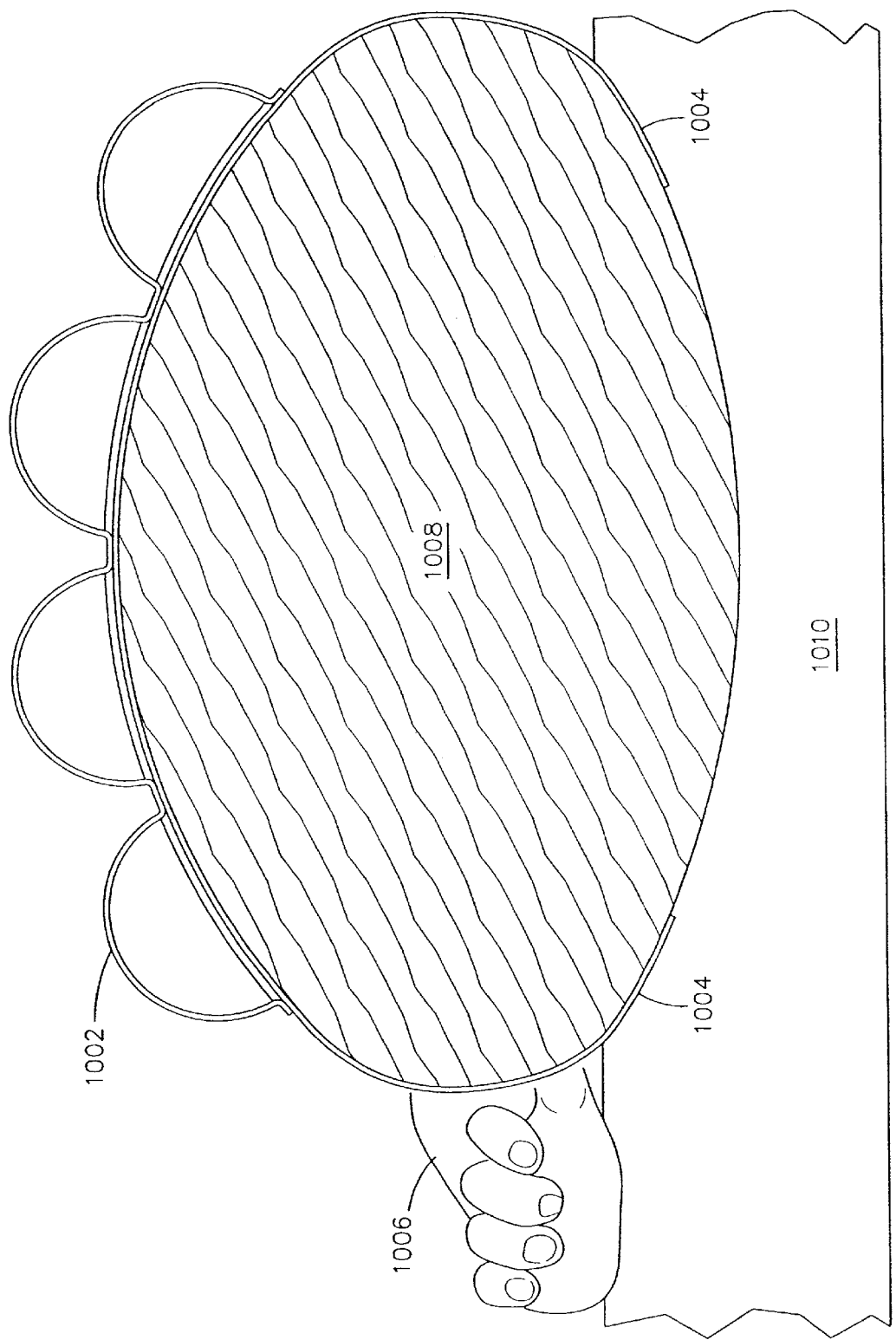
FIG. 10 is a cross-sectional side view of a cooling device held firmly in place by side drapes tucked under a person's body, according to the invention.

FIG. 10 shows the installation of an exemplary cooling device 1002 with torso drapes 1004. The drapes 1004 are tucked beneath the patient's torso 1008, and sandwiched between the torso 1008 and a support surface 1010 such as a bedding 1010. One of the patient's arms 1006 is shown for illustration. Although the patient's arms may be placed outside the torso drapes 1004 (as shown), they drapes may be tucked around the arms instead, if desired. The device may include features such as tear-out sections 124 (FIG. 1B), permitting the user to configure the device for arms-in or arms-out operation.

Figure 12:
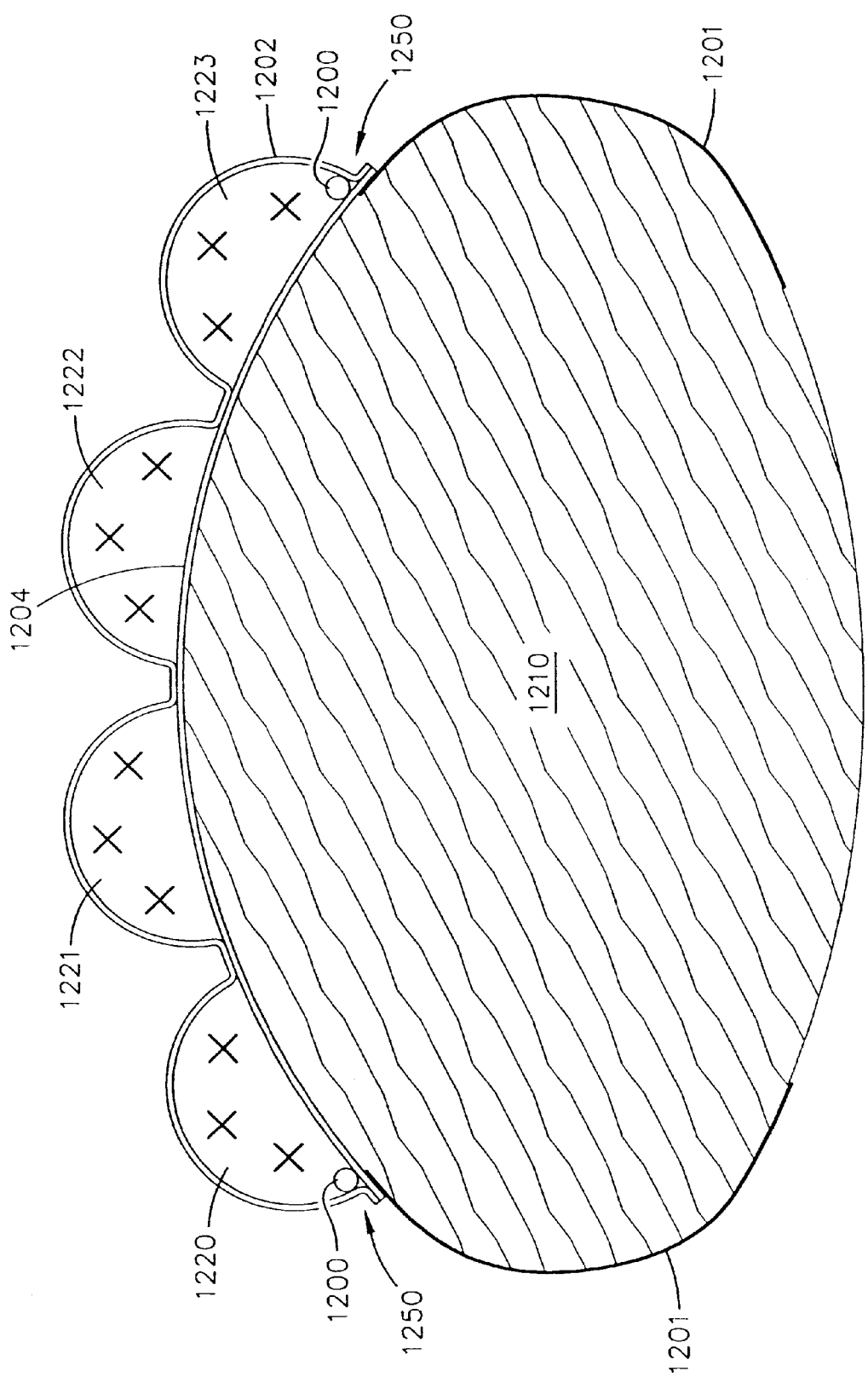
FIG. 12 is a cross-sectional side view of a cooling device with absorbent base sheet along with various anti-runoff features, according to the invention.

As another means to encourage thermal contact between the absorbent sheet and the patient, adhesive strips 1201 as shown in FIG. 12 may be used to pull the device tight against the patient's skin.

Self-Sealed Cooling Device

Figure 11:
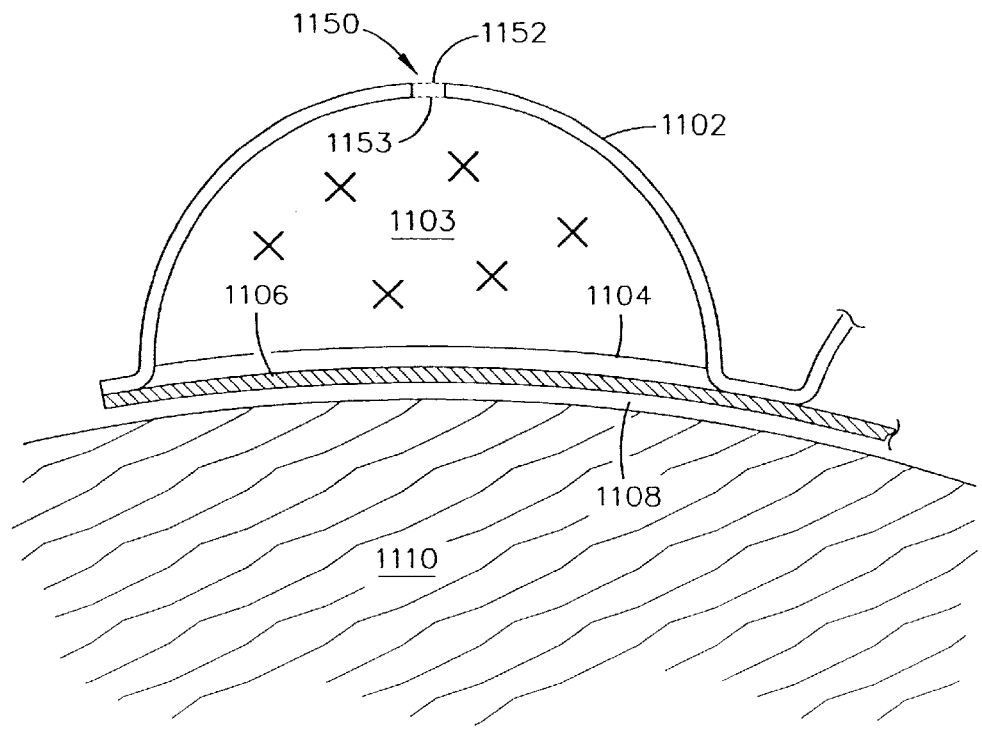
FIG. 11 is a cross-sectional side view of an inflatable cooling chamber employing an absorbent base sheet with various pro-contact features, according to the invention.

FIG. 11 depicts a different embodiment of cooling device, having a sealed interior structure. Beneficially, this structure helps prevent water runoff onto the patient, and also encourages thermal contact between the patient and the device. The device includes an upper sheet 1102 and absorbent base sheet 1104 comprising an evaporative cooling layer, as in previous embodiments.

In addition, the device includes a liquid impenetrable underlayer 1106 attached to the upper sheet 1102, thereby sealing the evaporative cooling layer 1104 in between. To form a complete seal, the underlayer 1106 is attached to the upper sheet 1102 around the perimeter of the device, at least. The underlayer 1106 may be additionally attached to the evaporative cooling layer 1104 in one or more places to ensure thermal contact between the layers 1104, 1106. The upper sheet 1102 and a liquid impenetrable underlayer 1106 cooperatively form a number of cooling chambers, such as 1103. As an example, the evaporative cooling layer 1104 may comprise gauze, a super-absorbent substance, or another water absorbent material, with the underlayer 1106 being laminated to the gauze. Optionally, the upper sheet 1102 may include an opening 1150 to provide for rewetting of the absorbent material. The opening 1150 may include, for example, membranes 1152–1153 to limit air escape while still permitting the introduction of wetting liquid.

The underlayer 1106 comprises a water impenetrable material that is capable of transferring heat between the body 1110 and the evaporative cooling layer 1104. For this reason, the underlayer 1106 may comprise a heat conductive material of any desired thickness, or a less heat conductive material of suitable thinness to avoid acting as a thermal insulator. Some examples are thin plastic or foil.

Moisture-laden air can escape from the chamber 1103 through air permeable regions in the upper sheet 1102, such as those described previously. This may be implemented by holes or naturally air permeable materials in the upper sheet 1102, evaporation openings in the connecting membrane between adjacent chambers, etc.

To further encourage thermal contact between the device and person, medical staff may apply a preparation liquid to the patient before placing the device over the person. The preparation liquid fills insulating air pockets that would otherwise occur in gaps between the relatively flat underlayer 1106 and the patient's skin. Such gaps may arise due to body hair, contoured body features, etc. The preparation liquid may comprise a gel, oil, water, or other appropriate substance that is applied by rubbing, spraying, etc.

Advantageously, the seal between the underlayer 1106 and upper sheet 1102 isolates the water inside the chambers 1103 from the person's skin. This prevents accidental runoff, which might cause discomfort by wetting the patient's bed.

Runoff Pads

As an alternative to the sealed arrangement of FIG. 11, the device may be equipped with runoff pads as shown in FIG. 12. An upper sheet 1202 and evaporative cooling layer 1204 cooperatively form a number of inflatable cooling chambers 1220–1223, as described in previous embodiments. The chambers 1220 and 1223 are the outermost chambers. Each of the outermost chambers 1220, 1223 has an outermost seam 1250, where the upper sheet 1202 and evaporative cooling sheet 1204 join. An absorbent runoff pad 1200 is attached inside each outermost chamber 1220, 1223, proximate the respective outermost seam 1250.

The runoff pads 1200 are made from an absorbent material, such as cotton, open cell foam, gauze, etc. For greatest effectiveness, the pads 1200 may be elongated to longitudinally run along the entire seam between upper sheet and evaporative cooling layer. The pads 1200 may be formed as strips, rolls, tubes, or any other configuration. Additional runoff pads may be placed at the ends of each chamber 1220–1223 if desired. The runoff pads prevent water from escaping the region where the person's skin contacts the device, and possibly running onto the persons' bed. The area of cooling focus, including the region of contact between the skin and the device, forms a "cooling field."

Specific Example

Figure 14B:
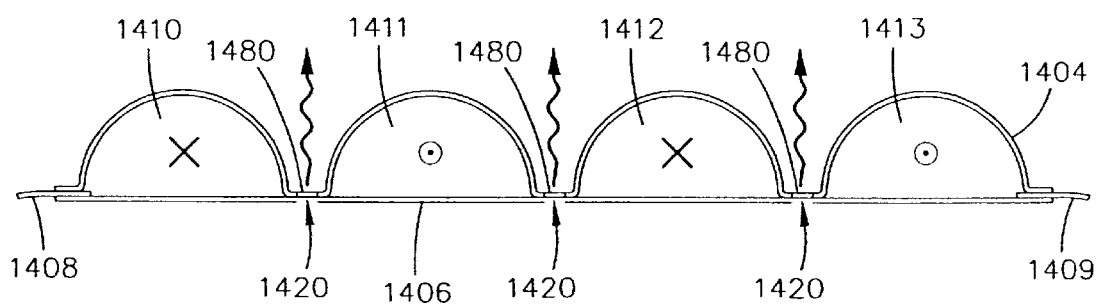
FIG. 14B is a cross-sectional side view of the cooling device of FIG. 14A.
Figure 14A:
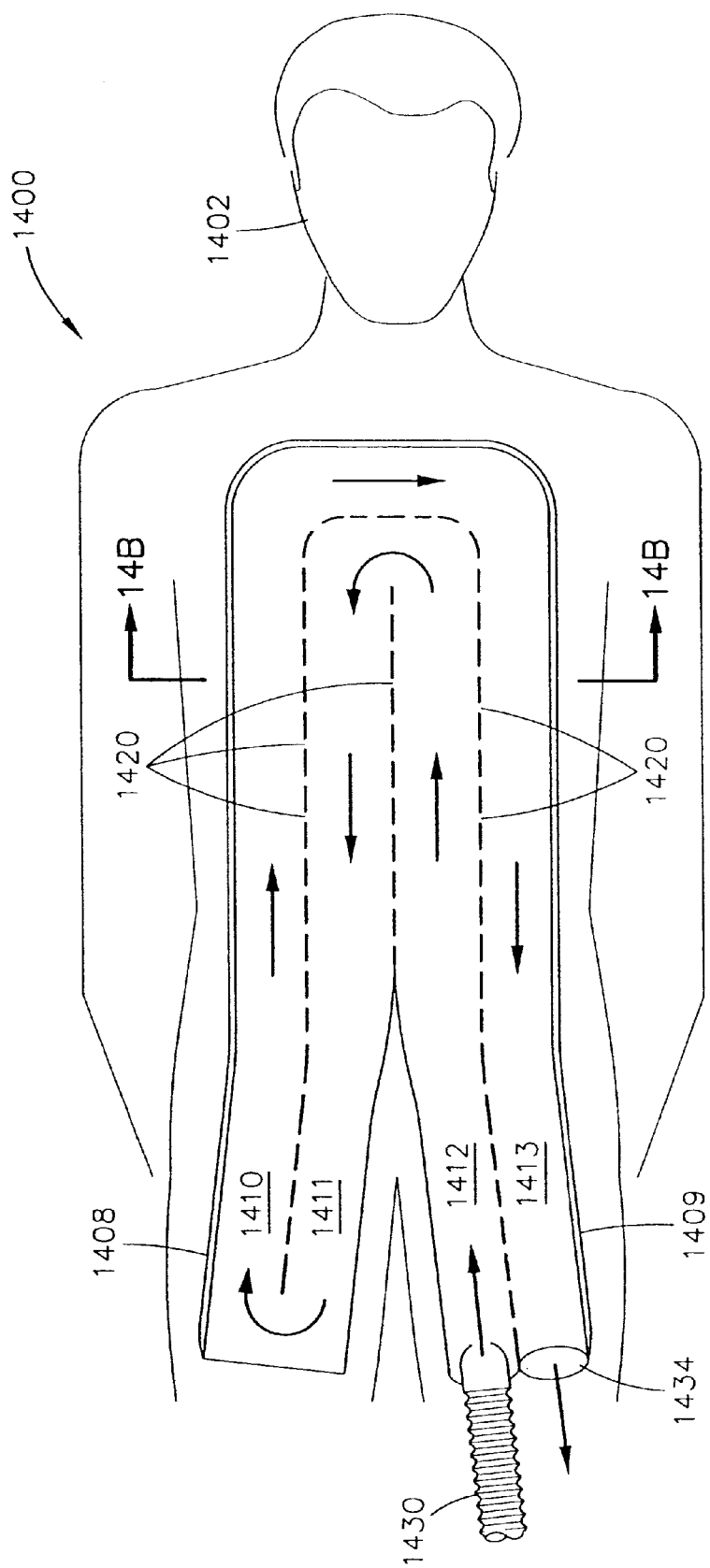
FIG. 14A is a top view of a reduced size cooling device utilizing U-shaped inflatable cooling chambers, according to the invention.

Having described various features relating to cooling devices utilizing the integrated absorbent sheet, reference is made to FIGS. 14A–14B to illustrate one exemplary embodiment of device including several such features. This embodiment provides a reduced size cooling device 1400 utilizing U-shaped inflatable cooling chambers. The device 1400 is shown relative to a persons' body 1402.

As best shown in FIG. 14B, the device includes an upper sheet 1404 coupled to an absorbent base sheet 1406 providing an evaporative cooling layer, as with embodiments previously described herein. The upper sheet 1404 and evaporative cooling sheet 1406 cooperatively form inflatable cooling chambers 1410–1413. Evaporation openings 1420 are defined in the upper sheet 1404 along the connecting membranes 1480 between adjacent chambers, permitting moisture-laden air to escape the chambers 1410–1413. Alternatively, instead of the evaporation openings as shown, the upper sheet may include punctures, holes, or other air permeable regions in the top or sides of the chambers to permit air to escape from the chambers directly through the upper sheet 1404.

The device 1400 also includes adhesive strips 1408–1409 to hold the device 1400 in thermal contact with the person 1402. In the illustrated embodiment, the adhesive strips 1408–1409 are sandwiched between the base sheet 1406 and upper sheet 1404 at their outermost junction.

The device 1400 receives air from an inlet hose 1430. Air travels through the chambers in the following sequence: 1412, 1411, 1410, and then 1413. Air exits the device at the outlet 1434.

Figure 14C:
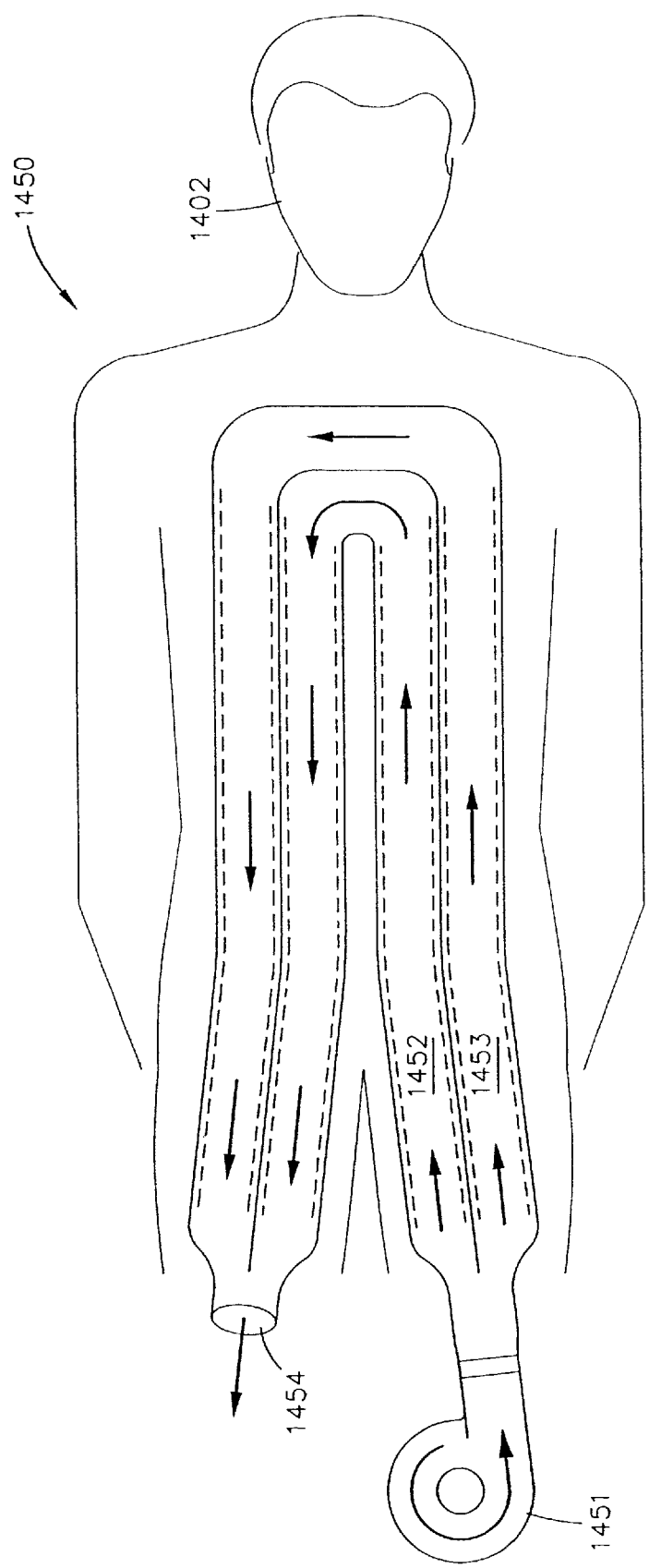
FIG. 14C is a top view of the device in FIG. 14A, showing an alternate fluid pathway.

FIG. 14C describes an alternative air pathway to the cooling device 1400. Namely, the device 1450 includes two inflatable chambers 1452–1453 in parallel. The air source 1451 directs air into the chambers 1452–1453, whereupon the air winds through the chambers in parallel and ultimately exits at the outlets 1454.

General Design/Implementation Considerations

A number of general concerns and design considerations may be considered in implementing cooling devices according to this invention. One such concern is blanket placement. Where air first enters the wetted portion of a cooling blanket, the air is driest, and therefore promotes the most cooling. Thus, the location of the air inlet and wetted area of the blanket are preferably positioned to place the most effective cooling region in closest contact with the body core, as exemplified by FIGS. 14A and 14C. The core body area includes the torso, and optionally may include the upper thighs, while preferably avoiding the gonads. In most cases, cooling the outer extremities is less effective than cooling the same size area near the body core because vasoconstriction at the extremities reduces heat transferred from the body core. Relatedly, the present invention contemplates optionally placing the extremities in a warm environment while cooling the body core, in order to prevent widespread vasoconstriction while using the cooling devices described herein.

Another concern involves the cross-section and shape of cooling chambers. As recognized by the present inventors, air collects moisture as it flows along a confined flow path, eventually reaching a point of saturation where evaporative cooling will cease. Therefore, each cooling device design makes a compromise between the overall cross-section and the flow path length to avoid developing a saturated flow before the air reaches the cooling device's farthest point. A smaller cross-section, such as from smaller cooling chambers, will reach saturation more quickly because the water vapor has a shorter path from the wetted surface across the flow to the free stream. Enlarging the cross-section in a "vertical" direction, away from the wetted surface, provides for a longer flow path before saturation, but reduces the cooling per unit area. More surface area of the body may be covered while shortening the total flow path length by using a manifold design with parallel paths (e.g., FIG. 14C) or a chamber cross-section that is wider across its base, where it contacts the body. The shorter flow path will deliver dryer air to the farthest ends of the flow path. Air velocity is reduced in the manifold, reducing cooling per unit area, but extending the cooling over a larger area at the same time.

OPERATION

Figure 15:
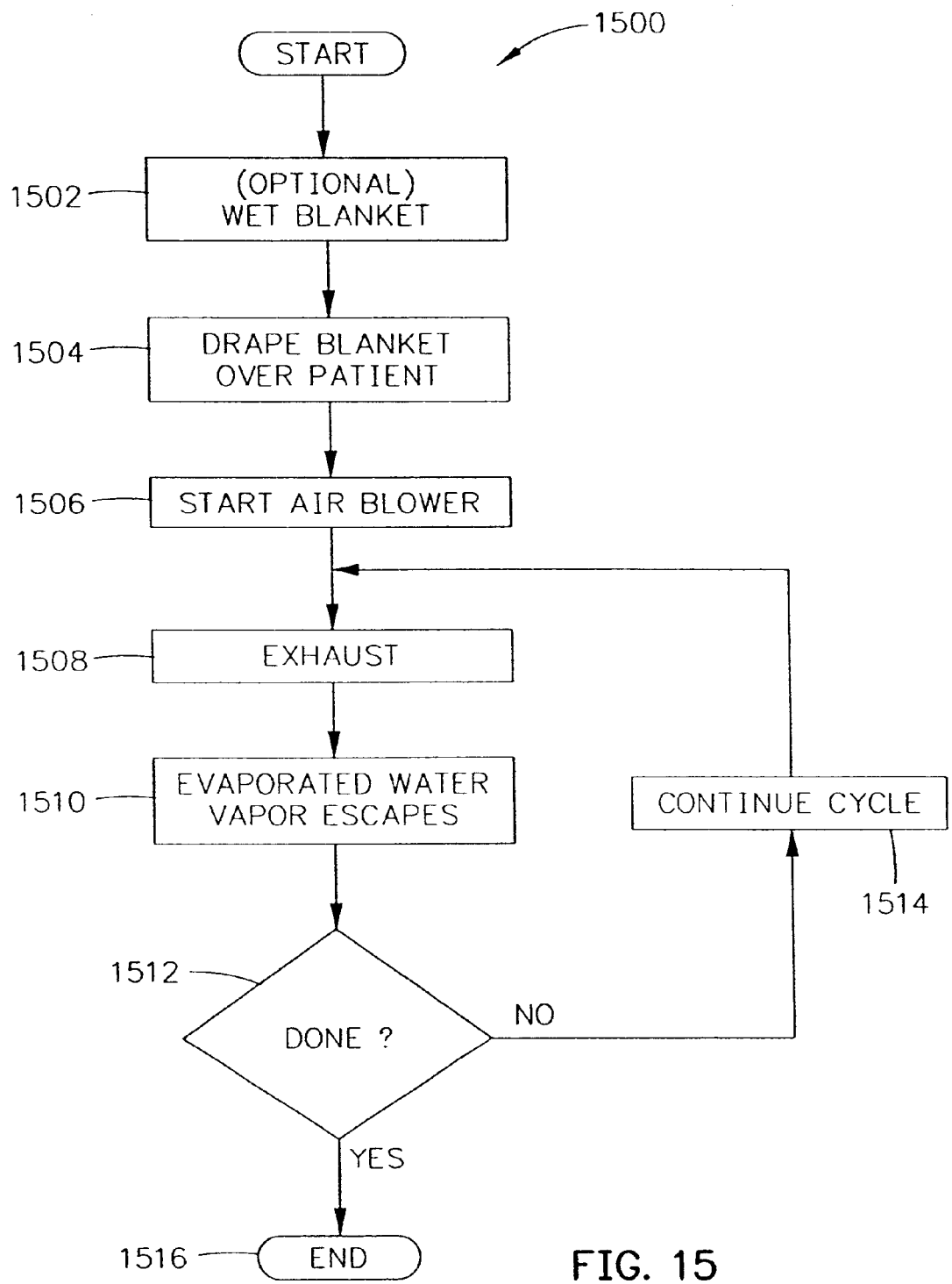
FIG. 15 is a flowchart of an operational sequence for using the cooling devices of this invention.

In addition to the various thermal cooling devices described above, a different aspect of the invention concerns appropriate methods for operating such equipment. FIG. 15 depicts a sequence 1500 for operating an inflatable cooling device. These steps 1500 may be performed by various people, depending upon the environment where the cooling device is used. For example, the steps 1500 may be performed by the subject or a family member at home, by attendants at a nursing facility, medical staff at a hospital, therapists at a treatment center, etc.

In step 1502, the operator moistens the device to facilitate evaporative cooling. This step is optional, since it is only applicable if the device includes an absorbent sheet (e.g., 506 from FIG. 5, or 602 from FIG. 6). The absorbent sheet may be moistened with water or another sufficiently volatile wetting liquid that is suitably hypoallergenic, effective in cooling, safe, etc. An antibacterial agent may be added to the wetting liquid if desired. For explanatory purposes, water is discussed as an exemplary wetting liquid. Step 1502 may be performed by running water over the absorbent sheet, soaking the absorbent sheet, immersing the absorbent sheet, irrigating the absorbent sheet with appropriate plumbing, spraying the absorbent sheet, or otherwise wetting the absorbent sheet. When the absorbent sheet is moistened, it expands. In the case of the device from FIG. 6, the expanding absorbent sheet may fill any pockets defined by the boundary layers 600, 604. If desired, step 1502 may be delayed until another time, such as after the device has already been draped over the person or after the air blower has been turned on.

Next, the operator drapes the device over a supine person, arranges the device, and configures the device further if necessary (step 1504). For greatest cooling, the person should be unclothed. If the device includes slits (e.g., 302–310 of FIG. 3), the device soon begins to conform to the person as exemplified by FIG. 4. Namely, the slits 302–305 permit the arm flaps 360, 370 to longitudinally bend around the person's outstretched arms. Similarly, the slits 306–310 permit the cutout leg flaps 380, 390 to laterally bend about the person's legs. This especially beneficial when the device is used to cool the person's skin by conduction, where thermal contact with the skin is critical. Also in step 1504, the operator may utilize torso, leg, arm, or other drapes by tucking them beneath the patient. The operator may also remove appropriate tear-out sections (e.g., 124, FIG. 1B) to configure the device for arms-in or arms-out operation as desired.

Next, the operator starts a fan or other air blower (not shown) that directs inlet air into the interior of the device's inflatable chambers (step 1506). Depending upon the particular application, inlet air may be room air, filtered air, heated or cooled air, or dehumidified air. In the case of non-absorbent cooling devices (e.g., FIGS. 1–2 as shown), step 1508 is performed next. In step 1508, inlet air from the interior of the cooling chamber(s) is exhausted onto the patient through the exhaust holes 200 in the base sheet. Also, in the embodiment of FIGS. 1–2, air circulation among the chambers 106 is aided by the ventilating cross-members 108. Air exhausted onto the patient encourages evaporation of moisture from the patient's body, helping to cool the patient.

In contrast, rather than exhausting air onto the person, devices with the absorbent base sheet perform the "exhaust" step 1508 by flowing air onto the absorbent base sheet itself, rather than the patient. Devices with absorbent base layers need not exhaust air onto the patient, since they operate by evaporative cooling the absorbent base layer, and cooling the patient's skin by thermal conduction.

After step 1508, water-laden air escapes the cooling device in step 1510. With a non-absorbent device as shown in FIG. 1, step 1510 occurs when air moistened by vapor from the person's skin escapes through the evaporation openings 110, thereby cooling the person's skin. With devices having absorbent base sheets, step 1510 occurs when air moistened by water from the absorbent sheet exits through the evaporation openings (e.g., 705, 1312), evaporatively cooling the absorbent base sheet itself. And because the absorbent base sheet thermally contacts the person's skin, the cooled base sheet cools the person's skin by conduction.

Next, step 1512 determines whether to stop the procedure. An operator may decide to end this procedure, for example, because the cooling goal has been achieved. Alternatively, the operator may need to remove the cooling device to facilitate surgery, re-position the person, permit the person to exercise, etc. If the cooling operation is not yet finished, the cooling cycle continues in step 1514. Otherwise, step 1512 proceeds to step 1516, where the routine 1500 ends. At this point, the operator may dispose of the entire thermal device 100. Alternatively, the operator may remove the absorbent base sheet (if detachable) and reuse the inflatable portion with a new or recycled/sterilized base sheet.

OTHER EMBODIMENTS

While the foregoing disclosure shows a number of illustrative embodiments of the invention, it will be apparent to those skilled in the art that various changes and modifications can be made herein without departing from the scope of the invention as defined by the appended claims. Furthermore, although elements of the invention may be described or claimed in the singular, the plural is contemplated unless limitation to the singular is explicitly stated.

Additionally, although the present disclosure is described in the context of humans, the invention additionally contemplates application of cooling techniques described herein to animals and other warm blooded animals. Moreover, ordinarily skilled artisans will recognize that operational sequences must be set forth in some specific order for the purpose of explanation and claiming, but the present invention contemplates various changes beyond such specific order.

What is claimed is:

1. A device for cooling a person, comprising:
   a first sheet; and
   a second sheet joined to the first sheet to form an inflatable structure; the inflatable structure including:
      an inlet for directing a flow of air into the inflatable structure;
      at least one exhaust region through at least one of the first sheet and the second sheet; and
      absorbent means for disposing an evaporable liquid in contact with the second sheet;
      the absorbent means disposed for being cooled by evaporation of the liquid in response to air exhausted from the inflatable structure through the exhaust region.

2. The device of claim 1, further comprising contact means for disposing the absorbent means in contact with a person.

3. The device of claim 2, wherein the contact means includes body drapes on opposite sides of the inflatable structure, the body drapes comprising a substantially flat, non-inflatable region.

4. The device of claim 3, wherein the body drapes are capable of being positioned beneath a person's body.

5. The device of claim 3, further comprising an adhesive layer attached to the body drapes to attach the cooling device to a person's body.

6. The device of claim 2, wherein the contact means includes pockets on opposite sides of the inflatable device.

7. The device of claim 1, wherein the absorbent means is attached to the second sheet.

8. The device of claim 1, wherein the absorbent means is an absorbent material.

9. The device of claim 1, wherein the absorbent means comprises upper and lower boundary layers sandwiching an absorbent material.

10. The device of claim 1, wherein the absorbent means is a super-absorbent material.

11. The device of claim 10, wherein the super-absorbent material is starch-grafted sodium polyacrylate.

12. The device of claim 1, wherein the inflatable structure includes:
   in regions where the sheets are not joined, one or more inflatable cooling chambers interconnected to define one or more inflatable, contiguous, interior regions;
   in regions where the sheets are joined, connecting membranes located between the chambers; and
   each connecting membrane including one or more evaporation openings through both the first and second sheets.

13. The device of claim 12, wherein the inflatable cooling chambers cooperatively define a single interior region having a serpentine shape having a beginning and an end, the inlet is located at the beginning, and the cooling device further includes an outlet provided at the end.

14. The device of claim 1, wherein the inflatable structure includes:

in regions where the sheets are not joined, one or more inflatable cooling chambers;

in regions where the sheets are joined, connecting membranes located between the chambers;

ventilating cross-members interconnecting the cooling chambers; and each connecting membrane including one or more evaporation openings through both the first and second sheets.

15. A system for cooling a person, comprising:

an upper sheet and a base sheet adhered in locations such that the sheets cooperatively form an inflatable structure that includes:

a plurality of elongated inflatable cooling chambers;

one or more connecting membranes between at least some neighboring cooling chambers; and ventilating cross-members interconnecting the cooling chambers;

an inlet into the inflatable structure;

a plurality of air permeable exhaust regions in the base sheet to pass pressurized air from inside the inflatable structure outward through the base sheet; and an evaporative cooling layer abutting the base sheet for being cooled by pressurized air passed through the air permeable exhaust regions.

16. The system of claim 15, wherein each connecting membrane includes one or more evaporation openings through both the upper and lower sheets.

17. The system of claim 15, wherein the inflatable structure includes a number of body-contour slits extending inward from a perimeter of the inflatable structure, where the slits have locations permitting the inflatable structure to conform to a person's legs and arms.

18. The system of claim 15, further comprising body drapes on opposite sides of the inflatable structure, each body drape comprising a substantially flat, non-inflatable region.

19. The system of claim 18, wherein the body drapes are capable of being positioned beneath a person's body.

20. The system of claim 15, wherein the inflatable structure includes pockets on opposite sides of the inflatable structure.

21. The system of claim 15, wherein the evaporative cooling layer is an absorbent material.

22. The system of claim 15, wherein the evaporative cooling layer is attached to the base sheet.

23. The system of claim 15, wherein the evaporative cooling layer comprises upper and lower boundary layers sandwiching an absorbent material.

24. The system of claim 15, wherein the evaporative cooling layer is a super-absorbent material.

25. The system of claim 24, wherein the super-absorbent material is starch-grafted sodium polyacrylate.

26. The system of claim 15, further comprising a liquid delivery tube coupled to the evaporation cooling layer.

27. A cooling device, comprising:

an upper sheet and an absorbent base sheet adhered in locations such that the sheets cooperatively form an inflatable structure that includes:

in regions where the sheets are not adhered, one or more inflatable cooling chambers interconnected to define one or more inflatable, contiguous, interior regions; and in regions where the sheets are adhered, connecting membranes located between the chambers;

at least one inlet for directing a flow of air into the inflatable structure;

one or more evaporation openings in the connecting membranes; and a plurality of air permeable exhaust regions in the absorbent base sheet located along each cooling chamber.

28. The device of claim 27, wherein the inflatable cooling chambers cooperatively define a single interior region having a serpentine shape having a beginning and an end, the inlet is located at the beginning, and the cooling device further includes an outlet provided at the end.

29. The device of claim 27, further comprising a liquid delivery tube coupled to the absorbent base sheet.

30. The device of claim 27, wherein the inflatable structure includes multiple inflatable cooling chambers defining multiple substantially parallel interior regions.

31. The device of claim 27, wherein each interior region defining a path having a beginning and an end, the inlet being located at the beginning, and an outlet provided at the end.

32. The device of claim 27, wherein the absorbent base sheet comprises a gauze material.

33. The device of claim 27, wherein the evaporation openings are through both the upper sheet and absorbent base sheet.

34. The device of claim 27, where the evaporation openings are provided by holes defined in the upper sheet.

35. The device of claim 27, further comprising an adhesive layer attached to the cooling device to attach the cooling device to a person's body.

36. The device of claim 27, wherein the inflatable structure includes a number of body-contour slits extending inward from a perimeter of the inflatable structure, where the slits have locations permitting the inflatable structure to conform to a person's legs and arms.

37. The device of claim 27, further comprising body drapes on opposite sides of the inflatable structure, each body drape comprising a substantially flat, non-inflatable region.

38. The device of claim 37, wherein the body drapes are capable of being positioned beneath a person's body.

39. The device of claim 37, the inflatable structure includes pockets on opposite sides of the inflatable structure.

40. The device of claim 37, further comprising a water impenetrable underlayer attached to the upper sheet to seal the absorbent base sheet therebetween.

41. The device of claim 40, the underlayer comprising a plastic layer adhered to the absorbent base sheet.

42. The device of claim 40, wherein the underlayer has heat conduction properties superior to air.

43. The device of claim 27, further comprising a liquid delivery tube coupled to the absorbent base sheet.

* * * * *